(12) United States Patent
Gilmer et al.

(10) Patent No.: US 11,179,380 B2
(45) Date of Patent: Nov. 23, 2021

(54) COMPOUNDS AND COMPOSITIONS FOR USE IN TREATING PSORIASIS

(71) Applicants: SOLVOTRIN THERAPEUTICS LTD, Cork (IE); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN

(72) Inventors: John Francis Gilmer, Dublin (IE); Mark Ledwidge, Cork (IE); Pat O'Flynn, Cork (IE); Francis Quilty, Westmeath (IE); Kate O'Donnell, Lough (IE)

(73) Assignees: SOLVOTRIN THERAPEUTICS LTD, Cork (IE); THE PROVOST, FELLOWS, FOUNDATION SCHOLARS, AND THE OTHER MEMBERS OF BOARD, OF THE COLLEGE OF THE HOLY AND UNDIVIDED TRINITY OF QUEEN ELIZABETH, NEAR DUBLIN, Dublin (IE)

( * ) Notice: Subject to any disclaimer, the term of this patent is extended or adjusted under 35 U.S.C. 154(b) by 9 days.

(21) Appl. No.: 16/496,778

(22) PCT Filed: Mar. 22, 2018

(86) PCT No.: PCT/EP2018/057382
§ 371 (c)(1),
(2) Date: Sep. 23, 2019

(87) PCT Pub. No.: WO2018/172496
PCT Pub. Date: Sep. 7, 2018

(65) Prior Publication Data
US 2021/0106576 A1    Apr. 15, 2021

(30) Foreign Application Priority Data

Mar. 24, 2017 (GB) .................................. 1704759

(51) Int. Cl.
*A61K 31/455* (2006.01)
*A61P 17/06* (2006.01)
*A61K 9/00* (2006.01)

(52) U.S. Cl.
CPC .......... *A61K 31/455* (2013.01); *A61K 9/0014* (2013.01); *A61P 17/06* (2018.01)

(58) Field of Classification Search
CPC ...... A61K 31/455; A61K 9/0014; A61P 17/06
(Continued)

(56) References Cited

U.S. PATENT DOCUMENTS

2012/0082634 A1* 4/2012 Ledwidge ............ A61K 31/404
424/78.01

FOREIGN PATENT DOCUMENTS

GB        1015800    *  1/1966
WO    WO-2012/017321 A2    2/2012

OTHER PUBLICATIONS

Tang et al., "The psoriasis drug monomethylfumarate is a potent nicotinic acid receptor agonist", Biochemical and Biophysical Research Communications, vol. 375, No. 4, Oct. 31, 2008, pp. 562-565.
(Continued)

*Primary Examiner* — Taylor V Oh
(74) *Attorney, Agent, or Firm* — Foley & Lardner LLP

(57) ABSTRACT

Compounds and pharmaceutical compositions for use in the treatment of psoriasis are disclosed. Preferred compounds have demonstrated efficacy in reducing skin scaling, erythema and skin thickness in the mouse model of Aldara-induced psoriasis.

16 Claims, 17 Drawing Sheets

(58) Field of Classification Search
USPC .......................................................... 514/355
See application file for complete search history.

(56) References Cited

OTHER PUBLICATIONS

Van Cauwenberghe, "Treatment of psoriasis with aspirin", Jan. 1, 1951 Elsevier Science Publishers, Amsterdam, NL.
International Search Report and Written Opinion issued in PCT Application No. PCT/EP2018/057382 dated Jun. 19, 2018, 10 pages.

* cited by examiner

Vehicle 0.5% ST0702

5% ST0702

Vehicle

ST0701

ST0703

Vehicle

ST0702Sal

COMPOUNDS AND COMPOSITIONS FOR USE IN TREATING PSORIASIS

CROSS-REFERENCE TO RELATED APPLICATION

This application is a national stage entry under 35 U.S.C. § 371 of International Patent Application No. PCT/EP2018/057382, filed Mar. 22, 2018, which in turn claims priority to Great Britain Application No. 1704759.8, filed Mar. 24, 2017, the entire content of each of which is incorporated herein by reference.

The present invention relates to compounds and compositions for use in the treatment of psoriasis.

BACKGROUND TO THE INVENTION

Psoriasis is a prevalent (2-3%) autoimmune disease in which pro-inflammatory cytokines such as TNFα mediate immune cell dysregulation in the dermis and ultimately cause rapid keratinocyte proliferation and migration. Keratinocytes may proliferate in response to cytokines such as TNFα, IL-17, IFN-γ, and IL-22 to accelerate loss of surface keratinocytes and direct migration of new T cell subsets and other immune effector cells into the skin. Whereas normal keratinocyte migration from the basal cell layer to the stratum corneum of the epidermis takes up to one month, in psoriasis this can occur over 3-4 days. The resultant excessive thickening of the epidermis with layers of immature keratinocyte produces thickened plaques with erythema due to increased vascularity. Patients experience the resulting plaques as emotionally and physically debilitating and consequently psoriasis has a significant effect on the sufferers' quality of life.

The condition affects males and females equally, shows evidence of genetic predisposition and usually appears in late teens or later in life.

Up to one quarter of patients also suffer from arthritis and other comorbidities include depressive illness, diabetes and cardiovascular disease. Factors known to aggravate the condition include smoking, high alcohol consumption, poor diet (high sugar), emotional stress and certain medications (for example, beta-blockers, lithium and anti-malarials).

The diagnosis is made clinically and the form of psoriasis is normally sub-categorised into several forms:
Plaque psoriasis
Guttate psoriasis
Flexural psoriasis
Nail psoriasis
Generalised pustular psoriasis
Palmoplantar pustulosis
Erythrodermic psoriasis Plaque psoriasis is the most prevalent form (80% of sufferers) and red plaques are covered with silvery scales, usually found on the elbows, knees, lower back and scalp. The majority of these patients have mild-moderate disease severity. Guttate psoriasis describes many small (up to 1 cm) red plaques on the trunk and limbs, often appearing after streptococcal or viral respiratory infection. Flexural psoriasis is the term used for red, smooth, continuous lesions found in the skin folds. Nail psoriasis describes pitting and nail dystrophy and occurs frequently in patients suffering with other forms of disease. Generalised pustular psoriasis is associates with fever and sterile pustules on painful red skin. Palmoplantar pustulosis is where these sterile pustules arise on palms and soles. Finally, erythrodermic psoriasis is a severe illness affecting most of the body surface and leads to hypothermia and can cause heart failure.

In addition to the sub-classifications above, disease severity in psoriasis is usually defined by how much of the body surface is affected and how much the illness and symptoms impact on quality of life. For example, psoriasis affecting the hands, feet and face is particularly debilitating:
Mild psoriasis: <5% of the body surface area and/or minimal impact on quality of life
Moderate psoriasis: 5-10% of the body surface area and/or moderate impact on quality of life
Severe psoriasis: >10% of the body surface area and/or severe impact on quality of life Approximately 70-80% of psoriasis is classified as mild-moderate and is managed using topical therapies because parenteral therapies, including newer agents directed at IL-17 and IL-23, are indicated in severe disease only. However, all current topical therapies have limitations.

The most effective topical therapy in mild-moderate disease is corticosteroid based, either alone (with emollients) or in combination with other topical therapies. However, long term side effects with topical corticosteroids are well known, especially with higher potency steroids: absorption through the skin can cause adrenal suppression, spreading or worsening of infection, acne or rosacea, thinning of the skin, irreversible striae and telangiectasia, contact dermatitis, depigmentation and hypertricosis. In order to avoid these adverse effects, lower potency corticosteroids are preferred for limited periods especially on the face, on thin skin, or for treating infants. However, thick, chronic plaques on the hands and feet require high potency agents for long (up to 3 week) courses. Ointments are best but increase absorption and may have poorer patient preference. Tachyphylaxis resulting in decreasing efficacy and/or acute flare up when the corticosteroid treatment is withdrawn is a major limiting factor and is managed by limiting the use, potency and frequency of corticosteroids.

Calcipotriol is a vitamin D analogue and a commonly used therapy, which reduces proliferation of keratinocytes. However, it can cause concentration dependent itchiness and erythema of the skin, which limits its usefulness and efficacy, particularly in facial areas. While tolerance develops to these adverse effects, calcipotriol is used in low concentrations, takes some weeks to have an impact and (often) requires additional corticosteroid therapy to achieve a satisfactory response—in terms of efficacy and reduction of skin irritation. Hypercalcaemia and renal function need to be monitored, calcium and vitamin D supplements should be avoided and the treatment should be limited to a total dose of 5 mg of calcipotriol per week. The efficacy of calcipotriol can be reduced by sunlight/UV radiation.

Tazarotene is a topical retinoid, which has similar efficacy to calcipotriol, but can cause irritation, dryness and erythema of the skin, usually to a greater extent than the vitamin D analogues which have also demonstrated utility in the treatment of psoriasis. Treatment of normal skin, face and flexures should be avoided.

Dithranol is a hydroxyantrone, which is generally very irritating to the skin and also causes staining problems, requiring application under carefully applied dressings twice daily, usually in specialist settings (e.g. hospital clinics) because the treatment causes permanent staining on clothing and bathtubs. The dithranol is then removed using a tar bath and the patient subsequently exposed to UV radiation. It is not suitable for areas of thin skin (e.g. face) and can cause staining of the skin, hair and fingernails. For a small proportion of well-motivated patients with small areas of plaque psoriasis, dithranol 1% cream can be rubbed into the plaques and washed off after 10-30 minutes.

Salicylic acid alone is used as a topical descaling agent (2%-4% w/w), with a similar effect to urea 10% w/w. It can cause skin irritation. Coal tar is anti-priuritic and also can help to normalise the rate of keratin growth, either alone or in combination with salicylic acid, but the mechanism of action is not well known.

Tar preparations can be used in shampoo preparations or as a bath additive, but can have an unpleasant smell for patients and may cause skin irritation. Other scalp treatments can include calcipotriol solution with care needed not to exceed 60 mL of a 50 mcg/mL solution per week. Ketoconzole (2%) is sometimes used, but has limited efficacy.

Treatment of nail psoriasis is very difficult and usually ineffective—sometimes corticosteroid and calcipotriol scalp solutions are applied to the nail beds, but the efficacy is poor and the improvement, if any, takes months.

The efficacy of the standard topical therapies has been evaluated in the imiquimod (IMQ) mouse model of psoriasis. Topical application of IMQ on mouse skin leads to the rapid proliferation of plasmacytoid dendritic cells, keratinocyte proliferation and migration, keratinocyte increase in cytokine production, T cell accumulation as well as upregulation of IL-23/17A and inflammatory cytokines. In this model, increased thickness is due to hyperplasia of basal and suprabasal keratinocytes and it has been shown that thickness reduction is best with corticosteroids (clobetesol) and that other agents including calcipotriol, and tazoratene are ineffective. In fact, treatment with calcipotriol or tazarotene exacerbated the IMQ-induced increased thickness of both the epidermal and subcutaneous tissue.

More specialist treatments for the management of severe psoriasis in addition to the topical agents above usually include phototherapy, methotrexate, acetretin, ciclosporin, fumarates and biologic agents (anti-TNFalpha, IL-17, IL-23 agents) where the long term safety is under ongoing observations.

In summary, management of this common auto-immune disorder requires topical therapies for the 70-80% of patients with mild-moderate disease and topical therapies in combination with specialist referral for severe or refractory disease. All of the currently available topical therapies have limitations in terms of efficacy and tolerability and there is significant clinical need new topical therapies for psoriasis. Accordingly, the provision of effective treatments, and effective topical treatments in particular, is highly desirable. Furthermore the provision of easy to use treatments which improve patient compliance with reduced side effects is also highly desirable.

SUMMARY OF THE INVENTION

In one aspect, the present invention provides a compound having the formula:

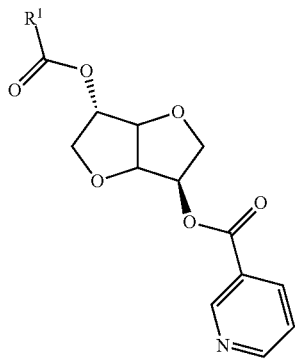

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, or a pharmaceutically acceptable salt thereof, for use in the treatment of psoriasis.

$R^1$ may be selected from methyl, ethyl, propyl, butyl, pentyl and hexyl, or isomers thereof.

Each $R^2$ and $R^3$ may independently be selected from methyl, ethyl, propyl, butyl, pentyl and hexyl, or isomers thereof.

The compound may have the formula:

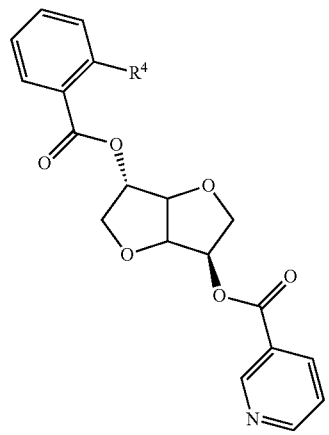

wherein $R^4$ is selected from H, hydroxyl or —O(O)$R^2$, wherein $R^2$ is $C_1$-$C_6$ alkyl, or a pharmaceutically acceptable salt thereof.

$R^2$ may be selected from methyl, ethyl, propyl, butyl, pentyl and hexyl, or isomers thereof.

Suitably, the compound is:

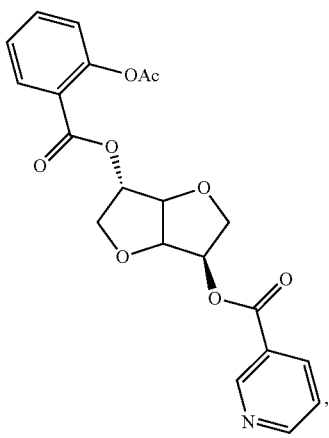 [SMILES: CC(=O)Oc1ccccc1C(=O)O[C@H]1COC2C1OC[C@H]2OC(=O)c1cccnc1]

or a pharmaceutically acceptable salt thereof.

The compound may be selected from the group consisting of:

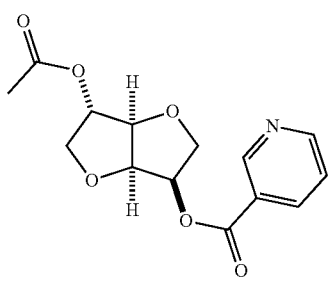

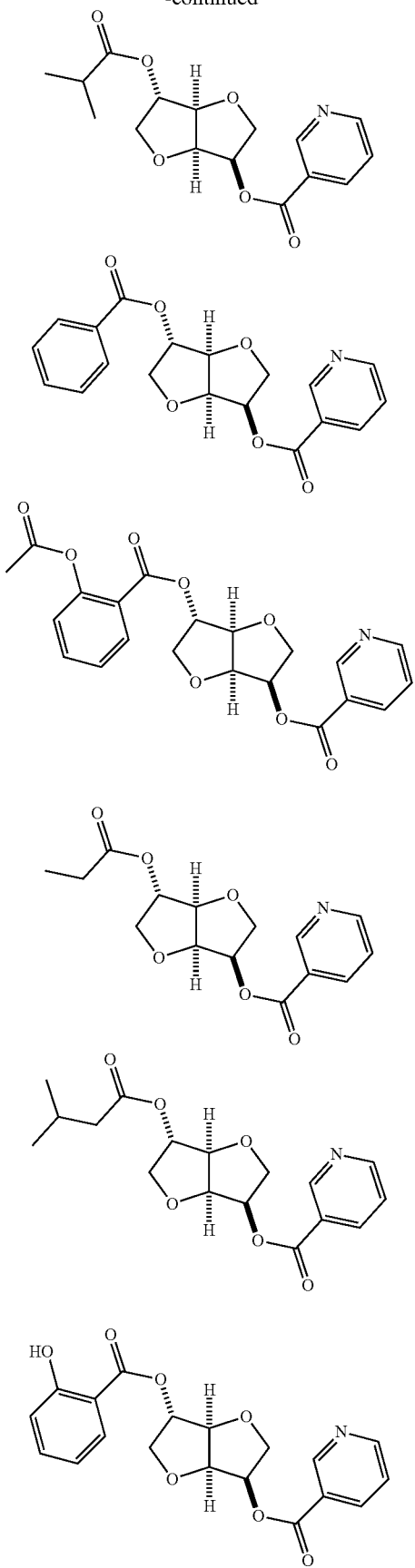

-continued

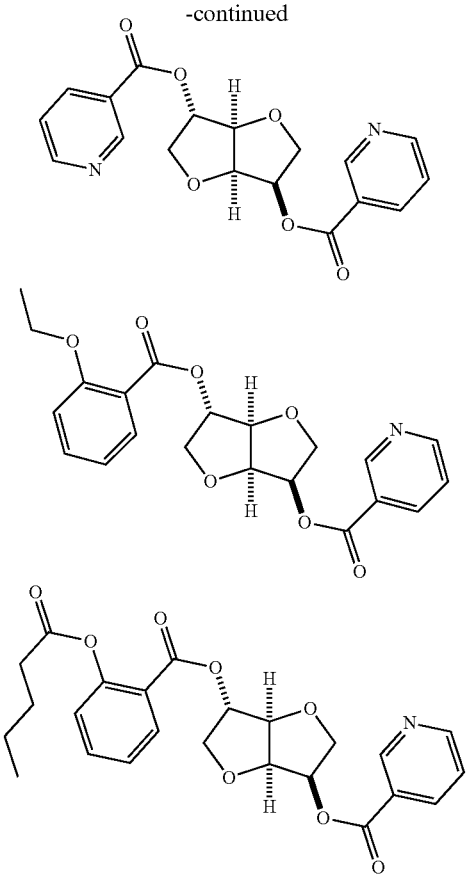

The compounds of the invention may suitably be in a pharmaceutically acceptable salt form.

In another aspect the present invention provides a pharmaceutical composition comprising a compound having the formula:

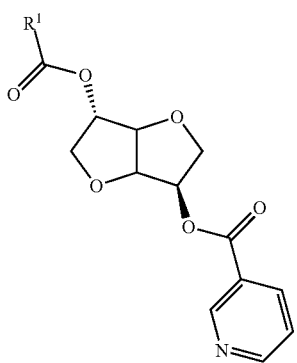

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3{}_2$, wherein $R^2$ is $C_1$-$C_6$ alkyl and wherein each $R^3$ is independently H or $C_1$-$C_6$ alkyl, and a pharmaceutically acceptable carrier or excipient, for use in the treatment of psoriasis.

$R^1$ may be selected from methyl, ethyl, propyl, butyl, pentyl and hexyl, or isomers thereof.

Each $R^2$ and $R^3$ may be independently selected from methyl, ethyl, propyl, butyl, pentyl and hexyl, or isomers thereof.

The compound may have the formula:

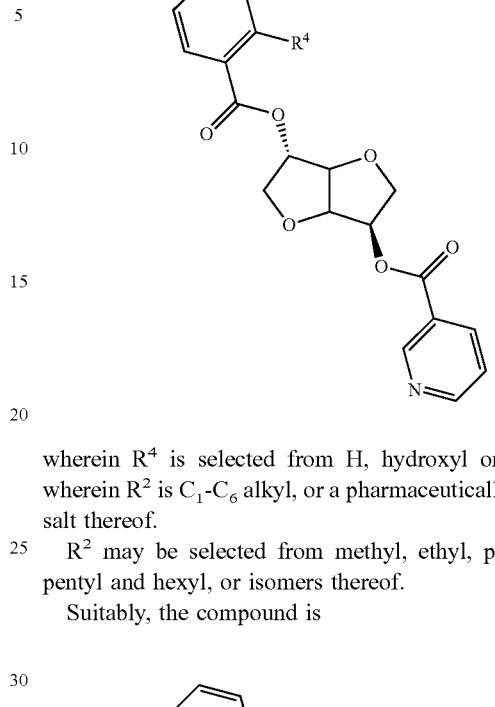

wherein $R^4$ is selected from H, hydroxyl or —O(O)$R^2$, wherein $R^2$ is $C_1$-$C_6$ alkyl, or a pharmaceutically acceptable salt thereof.

$R^2$ may be selected from methyl, ethyl, propyl, butyl, pentyl and hexyl, or isomers thereof.

Suitably, the compound is

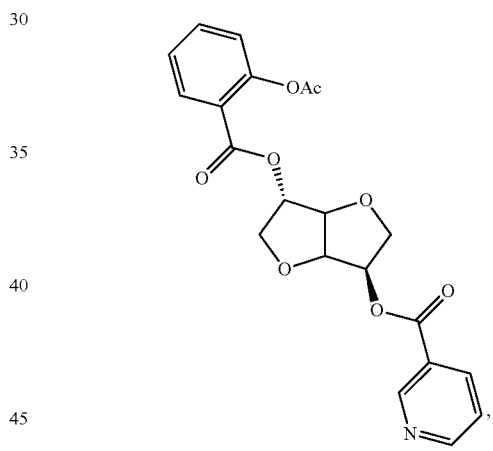

or a pharmaceutically acceptable salt thereof.

The pharmaceutical composition may be for topical administration.

The composition may be formulated as an ointment, cream, gel, solution, emulsion, dispersion, suspension, shampoo, paste, foam, aerosol, suppository, pad or gelled stick.

The pharmaceutical composition, may comprise a compound of the present invention in an amount of from 0.001 to 20 weight percent based on the total weight of the composition.

The pharmaceutical composition may comprise a compound of the present invention in an amount of from any of from about 0.01, 0.05, 0.1, 0.5, 1, 1.5, 2, 2.5, 3, 3.5, 4, 4.5, or 5 weight percent to an amount of from about 7.5, 10, 12.5, 15, 17.5 or 20 weight percent based on the total weight of the composition. For example, the compound may be present in an amount of from about 0.01 to about 10 weight percent, such as from about 0.01 to about 7.5 weight percent, or from about 0.1 to about 5 weight percent, such as from about 0.5 to 4.5 weight percent, or about 1 to about 3 weight percent based on the total weight of the composition.

Also disclosed herein is a method for treating psoriasis, the method comprising administering to a subject in need thereof a therapeutically effective amount of a compound having the formula:

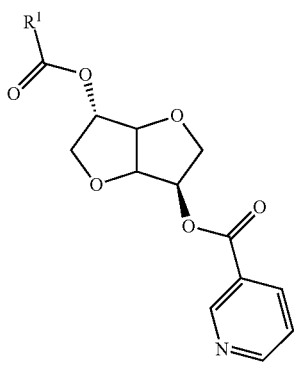

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, or a pharmaceutically acceptable salt thereof.

$R^1$ may be selected from methyl, ethyl, propyl, butyl, pentyl and hexyl, or isomers thereof.

Each $R^2$ and $R^3$ may be independently selected from methyl, ethyl, propyl, butyl, pentyl and hexyl, or isomers thereof.

The method may involve administering to a subject in need thereof administering a therapeutically effective amount of a compound having the formula:

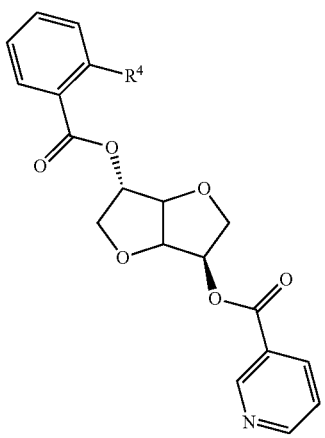

wherein $R^4$ is selected from H, hydroxyl or —O(O)$R^2$, wherein $R^2$ is $C_1$-$C_6$ alkyl, or a pharmaceutically acceptable salt thereof.

The compound may be

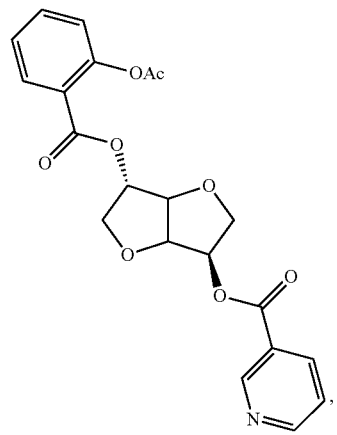 [SMILES: CC(=O)Oc1ccccc1C(=O)O[C@H]1COC2C1OC[C@H]2OC(=O)c1cccnc1]

or a pharmaceutically acceptable salt thereof.

The method for treating psoriasis may comprise administering to a subject in need thereof a pharmaceutical composition comprising a therapeutically effective amount of a compound having the formula:

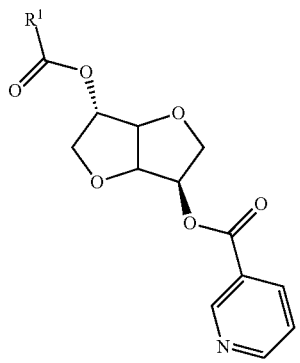

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, or a pharmaceutically acceptable salt thereof, and a pharmaceutically acceptable carrier or excipient.

$R^1$ may be selected from methyl, ethyl, propyl, butyl, pentyl and hexyl, or isomers thereof.

Each $R^2$ and $R^3$ may be independently selected from methyl, ethyl, propyl, butyl, pentyl and hexyl, or isomers thereof.

Alternatively, the method may involve administration to a subject in need thereof a pharmaceutical composition comprising a therapeutically effective amount of a compound having the formula:

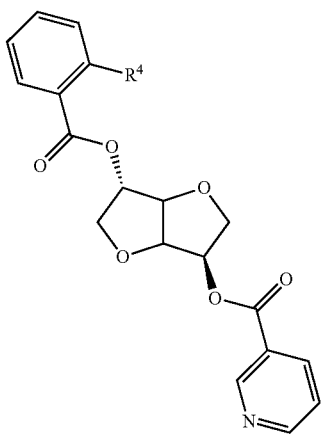

wherein R⁴ is selected from H, hydroxyl or —O(O)R², wherein R² is $C_1$-$C_6$ alkyl, or a pharmaceutically acceptable salt thereof, and a pharmaceutically acceptable carrier or excipient.

Suitably, the composition may comprise

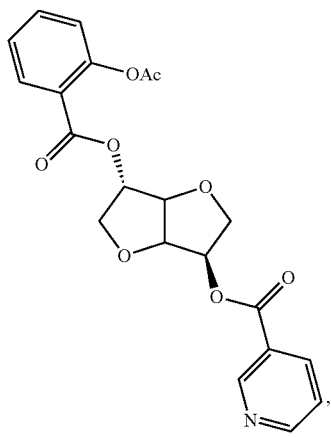 [SMILES: CC(=O)Oc1ccccc1C(=O)O[C@H]1COC2C1OC[C@H]2OC(=O)c1cccnc1]

or a pharmaceutically acceptable salt thereof.

In the method of the invention, the compound or pharmaceutical composition may be administered topically.

Also disclosed herein is use of a compound compound having the formula:

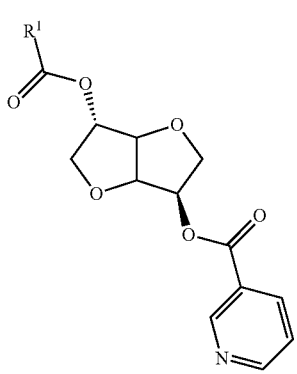

wherein R¹ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)R², NR³₂, wherein R² is $C_1$-$C_6$ alkyl and wherein each R³ is independently H or $C_1$-$C_6$ alkyl, or a pharmaceutically acceptable salt thereof, for the treatment of psoriasis.

R¹ may be selected from methyl, ethyl, propyl, butyl, pentyl and hexyl, or isomers thereof.

Each R² and R³ may be independently selected from methyl, ethyl, propyl, butyl, pentyl and hexyl, or isomers thereof.

The compound may have the formula:

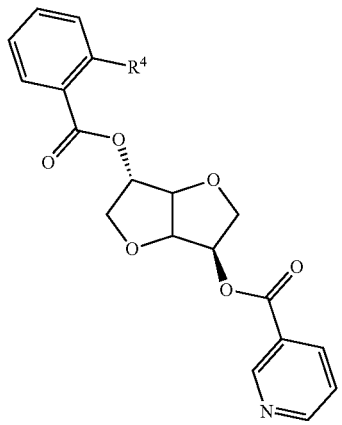

wherein R⁴ is selected from H, hydroxyl or —O(O)R², wherein R² is $C_1$-$C_6$ alkyl, or a pharmaceutically acceptable salt thereof.

The compound may be

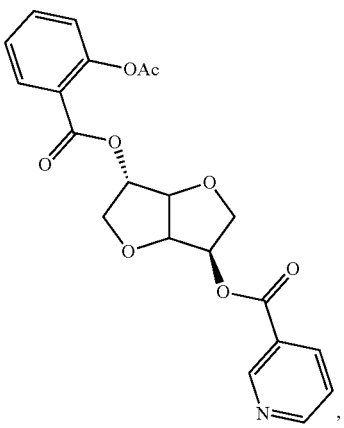 [SMILES: CC(=O)Oc1ccccc1C(=O)O[C@H]1COC2C1OC[C@H]2OC(=O)c1cccnc1]

or a pharmaceutically acceptable salt thereof.

BRIEF DESCRIPTION OF THE DRAWINGS

Embodiments of the invention will be described, by way of example only, with reference to the accompanying drawings in which.

DETAILED DESCRIPTION

Figure 1:
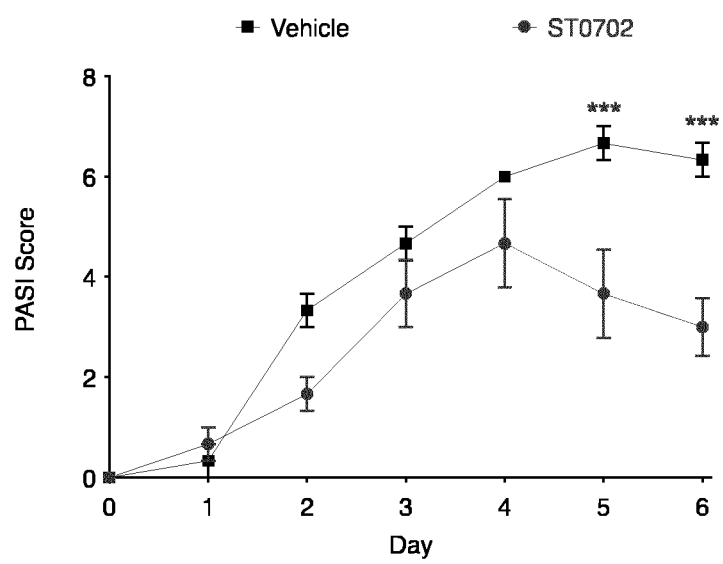
FIG. 1: Psoriasis Area and Severity Index (PASI) score of Aldara-treated mice exposed to Vehicle or 3% ST0702.

Before further description, certain terms employed in the specification, examples and appended claims are defined herein. These definitions should be read in light of the remainder of the disclosure and understood as by a person of skill in the art. Unless defined otherwise, all technical and scientific terms used herein have the same meaning as commonly understood by a person of ordinary skill in the art.

The term "pharmaceutically acceptable carrier" or "pharmaceutically acceptable excipient" as used herein refers to any of the following: solvents, dispersion media, coatings, isotonic and absorption delaying agents, with the proviso that they are compatible with pharmaceutical administration. The use of carriers and excipients for pharmaceutically active substances is well known to those skilled in the art. Furthermore, the compositions may further comprise other active compounds providing supplemental, additional, or enhanced therapeutic functions.

The term "pharmaceutical composition" as used herein refers to a composition comprising at least one compound as disclosed herein formulated together with one or more pharmaceutically acceptable carriers or excipients.

The compounds contemplated herein can be administered to a mammal, such as a human, but can also be administered to other mammals such as an animal, for example domestic animals, farm animals and laboratory animals, in need of veterinary treatment. The mammal treated in the methods contemplated herein is suitably a mammal with psoriasis.

As used herein, the term "therapeutically effective amount" refers to the amount of the compound in question that will elicit the desired biological or medical response in a tissue, system or animal (e.g., mammal or human). The compounds contemplated herein are administered to the "subject", "individual" or "patient", (which can be a mammal as described above), in therapeutically effective amounts to treat a disease or disorder. Alternatively, a therapeutically effective amount of a compound is the quantity required to achieve a desired therapeutic and/or prophylactic effect.

The term "pharmaceutically acceptable salt(s)" as used in this specification refers to salts of acidic or basic groups that may be present in compounds used in the compositions. Basic compounds of the contemplated herein are capable of forming a plethora of salts with various inorganic and organic acids. Pharmaceutically acceptable acid addition salts of such basic compounds are those that form non-toxic acid addition salts, i.e., salts containing pharmacologically acceptable anions, including, but not limited to any of the following: chloride, bromide, iodide, nitrate, sulfate, bisulfate, methanesulfonate, ethanesulfonate, benzenesulfonate, p-toluenesulfonate, phosphate, acid phosphate, malate, oxalate, nicotinate, isonicotinate, acetate, lactate, salicylate, citrate, tartrate, oleate, tannate, pantothenate, saccharate, formate, benzoate, bitartrate, ascorbate, succinate, maleate, gentisinate, fumarate, gluconate, glucaronate, glutamate, and pamoate (i.e., 1,1'-methylene-bis-(2-hydroxy-3-naphthoate)) salts.

Acidic compounds contemplated herein are capable of forming a plethora of pharmaceutically acceptable salts with various basic substances. For example, the pharmaceutically acceptable salts may include alkali metal or alkaline earth metal salts and, particularly, calcium, magnesium, sodium, lithium, zinc, potassium, and iron salts. Compounds comprising a basic or acidic moiety may also form pharmaceutically acceptable salts with amino acids. The compounds of the disclosure may contain both acidic and basic groups; for example, one amino and one carboxylic acid group. In such a case, the compound can exist as an acid addition salt, a zwitterion, or a base salt.

The compounds disclosed herein can exist in solvated as well as unsolvated forms, for example as hydrates or with other pharmaceutically acceptable solvents such as ethanol, and the like. The compounds disclosed herein embrace both solvated and unsolvated forms. The compound of the invention may be amorphous. The compound of the invention may exist as a single polymorph or as a mixture of polymorphs. In some embodiments, the compound of the invention is in a crystalline form.

The disclosure also embraces isotopically labelled compounds of the disclosure, wherein said isotopically labelled compounds are identical to the compounds of the invention except that one or more atoms are replaced by an isotopic variant. Isotopes that can be incorporated into compounds of the disclosure include isotopes of hydrogen, carbon, nitrogen, oxygen, phosphorus, sulfur, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. For example, a compound of the disclosure may have one or more hydrogen atoms replaced with deuterium.

Suitable compounds for use in the present invention include:

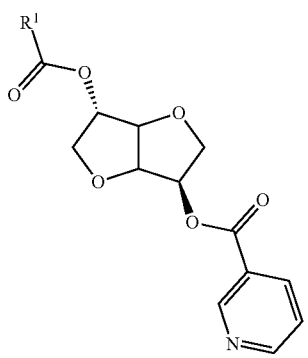

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3{}_2$, wherein $R^2$ is $C_1$-$C_6$ alkyl and wherein each $R^3$ is independently H or $C_1$-$C_6$ alkyl, or a pharmaceutically acceptable salt thereof.

$R^1$ may be selected from methyl, ethyl, propyl, butyl, pentyl and hexyl, or isomers thereof.

When $R^1$ is aryl, it may for example be phenyl or pyridyl, which may optionally be substituted with one or more of hydroxyl, halo, $C_1$-$C_6$ alkyl, $C_1$-$C_6$ alkoxy, —O(O)$R^2$, $NR^3{}_2$, wherein $R^2$ is $C_1$-$C_6$ alkyl and wherein each $R^3$ is independently H or $C_1$-$C_6$ alkyl.

Each $R^2$ and $R^3$ may be independently selected from methyl, ethyl, propyl, butyl, pentyl and hexyl, or isomers thereof.

CHEMISTRY

Isosorbide 2-acetate-5-mononitrate

Isosorbide mononitrate (mol. wt. 191.139 g/mol, 10 mmol, 1.91 g) was dissolved in dichloromethane (50 mL) in a 100 mL round bottomed flask. Triethylamine (mol. wt. 101.19 g/mol, d. 0.7255 g/mL, 11 mmol, 1.52 mL), 4-Dimethylaminopyridine (mol. wt. 122.17 g/mol, 2 mmol, 0.244 g), and acetic anhydride (mol. wt. 102.09 g/mol, d. 1.08 g/mL, 11 mmol, 1.04 mL) were added to the flask. The reaction mixture was stirred for 3 hours. The reaction was monitored by TLC (1:1 hexane:ethyl acetate) to observe the disappearance of the ISMN. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane and crystallisation using diethyl ether yielded a white powder (2.133 g, 91.54%) mol. wt. 233.18 g/mol.

Isosorbide 2-acetate

Isosorbide 2-acetate-5-mononitrate (mol. wt. 233.18 g/mol, 9.14 mmol, 2.133 g) was dissolved in ethyl acetate (30 mL) in a 100 mL round bottomed flask. A spatula tip full of 10% palladium on activated carbon was added to the solution. Air was expelled from the flask and the mixture was kept under an atmosphere of hydrogen gas. The mixture was stirred for 24 hours. The reaction was monitored by TLC (1:1 hexane:ethyl acetate) to observe the disappearance of the Isosorbide 2-acetate-5-mononitrate. Once complete, the reaction mixture was filtered through a fritted glass funnel to remove the catalyst. The solvent was evaporated under vacuum and crystallised using diethyl ether to give a white powder (1.55 g, 90%) mol. wt. 188.18 g/mol.

Isosorbide 2-acetate-5-nicotinate

Isosorbide 2-acetate (mol. wt. 188.18 g/mol, 2.65 mmol, 0.500 g) was dissolved in dichloromethane (30 mL) in a 100 mL round bottomed flask. Triethylamine (mol. wt. 101.19 g/mol, d. 0.7255 g/mL, 5.8 mmol, 0.810 mL), 4-Dimethylaminopyridine (mol. wt. 122.17 g/mol, 0.53 mmol, 0.065 g), and nicotinoyl chloride hydrochloride (mol. wt. 178.02 g/mol, 2.915 mmol, 0.52 g) were added to the flask. The reaction mixture was stirred for 24 hours. The reaction was monitored by TLC (1:1 hexane:ethyl acetate) to observe the disappearance of the starting material. After 24 hours, additional triethylamine (mol. wt. 101.19 g/mol, d. 0.7255 g/mL, 2.9 mmol, 0.405 mL), DMAP (mol. wt. 122.17 g/mol, 0.53 mmol, 0.065 g), and nicotinoyl chloride hydrochloride (mol. wt. 178.02 g/mol, 1.46 mmol, 0.260 g) were added to ensure completion of the reaction. Once complete, the dichloromethane was removed under vacuum. The crude product was then dissolved in DCM and purified by column chromatography, using hexane and ethyl acetate (1:1) as eluent. Once the solvent was evaporated off, the mixture was recrystallized with diethyl ether to yield a white crystalline powder (0.500 g, 64%) mol. wt. 293.28 g/mol. $^1$H NMR (CDCl$_3$) 2.07 (s, 3 H, H15) 3.90-4.06 (m, 4 H, H1/H6) 4.53 (d, J=4.88 Hz, 1 H, H3) 4.98 (t, J=5.19 Hz, 1 H, H4) 5.22 (d, J=3.05 Hz, 1 H, H2) 5.41 (q, J=5.29 Hz, 1 H, H5) 7.41 (dd, J=7.94, 4.88 Hz, 1 H, H12) 8.31 (dt, J=7.94, 1.83 Hz, 1 H, H13) 8.79 (dd, J=4.58, 1.53 Hz, 1 H, H11) 9.24 (d, J=1.83 Hz, 1 H, H9). $^{13}$C NMR ppm (CDCl$_3$): 20.53 43.89, 70.29, 73.08, 74.48, 76.36, 76.68, 77.55, 80.57, 85.76, 123.00, 125.08, 136.81, 150.60, 153.36, 164.21, 169.65.

Isosorbide 2-propionate-5-mononitrate

Isosorbide mononitrate (mol. wt. 191.139 g/mol, 10 mmol, 1.91 g) was dissolved in dichloromethane (50 mL) in a 100 mL round bottomed flask. Triethylamine (mol. wt. 101.19 g/mol, d. 0.7255 g/mL, 11 mmol, 1.52 mL), 4-Dimethylaminopyridine (mol. wt. 122.17 g/mol, 5 mmol, 0.61 g), and propionyl chloride (mol. wt. 92.522 g/mol, d. 1.065 g/mL, 11 mmol, 0.956 mL) were added to the flask. The reaction mixture was stirred for 4 hours. The reaction was monitored by TLC (1:1 hexane:ethyl acetate) to observe the disappearance of the ISMN. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane and crystallisation using diethyl ether yielded a white powder (2.1 g, 85%) mol. wt. 247.20 g/mol.

Isosorbide 2-propionate

Isosorbide 2-propionate-5-mononitrate (mol. wt. 247.20 g/mol, 5 mmol, 1.25 g) was dissolved in ethyl acetate (30 mL) in a 100 mL round bottomed flask. A spatula tip full of 10% palladium on activated carbon was added to the solution. Air was expelled from the flask and the mixture was kept under an atmosphere of hydrogen gas. The mixture was stirred for 6 hours. The reaction was monitored by TLC (1:1 hexane:ethyl acetate) to observe the disappearance of the Isosorbide 2-propionate-5-mononitrate. Once complete, the reaction mixture was filtered through a fritted glass funnel to remove the catalyst. The solvent was evaporated under vacuum and crystallised using diethyl ether to give a white powder (0.95 g, 93%) mol. wt. 202.21 g/mol.

Isosorbide 2-propionate-5-nicotinate

Isosorbide 2-propionate (mol. wt. 202.21 g/mol, 2.23 mmol, 0.450 g) was dissolved in dichloromethane (30 mL) in a 100 mL round bottomed flask. Triethylamine (mol. wt. 101.19 g/mol, d. 0.7255 g/mL, 4.9 mmol, 0.680 mL), 4-Dimethylaminopyridine (mol. wt. 122.17 g/mol, 0.223 mmol, 0.027 g), and nicotinoyl chloride hydrochloride (mol. wt. 178.02 g/mol, 2.453 mmol, 0.436 g) were added to the flask. The reaction mixture was stirred for 24 hours. The reaction was monitored by TLC (1:1 hexane:ethyl acetate) to observe the disappearance of the starting material. After 24 hours, additional triethylamine (mol. wt. 101.19 g/mol, d. 0.7255 g/mL, 2.45 mmol, 0.340 mL), DMAP (mol. wt. 122.17 g/mol, 0.223 mmol, 0.027 g), and nicotinoyl chloride hydrochloride (mol. wt. 178.02 g/mol, 1.227 mmol, 0.218 g) were added to ensure completion of the reaction. Once complete, the dichloromethane was removed under vacuum. The crude product was then dissolved in DCM and purified by column chromatography, using hexane and ethyl acetate (1:1) as eluent. Once the solvent was evaporated off, the mixture was recrystallized with diethyl ether to yield a white crystalline powder (0.51 g, 74.5%) mol. wt. 307.30 g/mol. $^1$H NMR (CDCl$_3$) δ: 1.14 (t, J=7.32 Hz, 3 H, H16) 2.35 (q, J=7.53 Hz, 2 H, H15) 3.92-4.09 (m, 4 H, H1/6) 4.54 (d, J=4.88 Hz, 1 H, H3) 4.99 (t, J=4.88 Hz, 1 H, H4) 5.25 (d, J=3.66 Hz, 1 H, H2) 5.42 (q, J=5.09 Hz, 1 H, H5) 7.42 (dd, J=7.94, 4.88 Hz, 1 H, H12) 8.33 (dt, J=8.09, 2.06 Hz, 1 H, H13) 8.81 (dd, J=4.58, 1.53 Hz, 1 H, H11) 9.25 (s, 1 H, H9). $^{13}$C NMR ppm (CDCl$_3$): 8.62, 20.33, 27.13, 70.28, 73.21, 74.56, 76.37, 76.69, 77.39, 80.60, 85.85, 112.10, 123.05, 136.89, 150.62, 153.36, 164.26, 173.15.

Isosorbide 2-butyrate-5-mononitrate

Isosorbide mononitrate (mol. wt. 191.139 g/mol, 10 mmol, 1.91 g) was dissolved in dichloromethane (50 mL) in a 100 mL round bottomed flask. Triethylamine (mol. wt. 101.19 g/mol, d. 0.7255 g/mL, 11 mmol, 1.52 mL), 4-Dimethylaminopyridine (mol. wt. 122.17 g/mol, 5 mmol, 0.61 g), and butyryl chloride (mol. wt. 106.55 g/mol, d. 1.026 g/mL, 11 mmol, 1.14 mL) were added to the flask. The reaction mixture was stirred for 4 hours. The reaction was monitored by TLC (1:1 hexane:ethyl acetate) to observe the disappearance of the ISMN. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane yielded a yellow oil (2.359 g, 90%) mol. wt. 261.23 g/mol.

Isosorbide 2-butyrate

Isosorbide 2-butyrate-5-mononitrate (mol. wt. 261.23 g/mol, 8.7 mmol, 2.28 g) was dissolved in acetic acid (20 mL) in a 100 mL round bottomed flask. Zinc powder (mol. wt. 65 g/mol, 87 mmol, 5.695 g) was added to the flask. The mixture was stirred for 6 hours. The reaction was monitored by TLC (1:1 hexane:ethyl acetate) to observe the disappearance of the Isosorbide 2-butyrate-5-mononitrate. Once complete, the reaction mixture was filtered through cotton wool to remove the catalyst. Ethyl acetate was then added to the reaction mixture and following this the mixture was washed with 1M HCl (50 mL), saturated sodium bicarbonate solution (50 mL), saturated brine solution (50 mL) and dried with anhydrous sodium sulphate (1 g). Evaporation of the ethyl acetate yielded a white powder (1.13 g, 60%) mol. wt. 216.23 g/mol.

Isosorbide 2-butyrate-5-nicotinate

Isosorbide 2-butyrate (mol. wt. 216.23 g/mol, 2.31 mmol, 0.500 g) was dissolved in dichloromethane (30 mL) in a 100 mL round bottomed flask. Triethylamine (mol. wt. 101.19 g/mol, d. 0.7255 g/mL, 5.08 mmol, 0.706 mL), 4-Dimethylaminopyridine (mol. wt. 122.17 g/mol, 0.231 mmol, 0.03 g), and nicotinoyl chloride hydrochloride (mol. wt. 178.02 g/mol, 2.541 mmol, 0.453 g) were added to the flask. The reaction mixture was stirred for 24 hours. The reaction was monitored by TLC (1:1 hexane:ethyl acetate) to observe the disappearance of the starting material. After 24 hours, additional triethylamine (mol. wt. 101.19 g/mol, d. 0.7255 g/mL, 2.54 mmol, 0.353 mL), DMAP (mol. wt. 122.17 g/mol, 0.231 mmol, 0.030 g), and nicotinoyl chloride hydrochloride (mol. wt. 178.02 g/mol, 1.27 mmol, 0.227 g) were added to ensure completion of the reaction. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane and crystallisation using diethyl ether yielded a white powder (0.5 g, 67.3%) mol. wt. 321.33 g/mol. $^1$H NMR (CDCl$_3$) δ: 0.75-0.87 (m, 3 H, H17) 1.53 (sxtd, J=7.45, 7.45, 7.45, 7.45, 7.45, 1.83 Hz, 2 H, H16) 2.20 (td, J=7.32, 1.83 Hz, 2 H, H15) 3.78-3.98 (m, 4 H, H1/H6) 4.44 (d, J=4.27 Hz, 1 H, H3) 4.82-4.92 (m, 1 H, H4) 5.14 (br. s., 1 H, H2) 5.25-5.38 (m, 1 H, H5) 7.27-7.38 (m, 1 H, H12) 8.14-8.26 (m, 1 H, H13) 8.64-8.76 (m, 1 H, H11) 9.14 (br. s., 1 H9). $^{13}$C NMR ppm (CDCl$_3$): 13.22, 17.98, 35.63, 70.27, 73.21, 74.54, 76.37, 76.68, 77.30, 80.58, 85.84, 123.03, 136.84, 150.61, 153.36, 164.25, 172.30.

Isosorbide 2-valeroate-5-mononitrate

Isosorbide mononitrate (mol. wt. 191.139 g/mol, 10 mmol, 1.91 g) was dissolved in dichloromethane (50 mL) in a 100 mL round bottomed flask. Triethylamine (mol. wt. 101.19 g/mol, d. 0.7255 g/mL, 11 mmol, 1.52 mL), 4-Dimethylaminopyridine (mol. wt. 122.17 g/mol, 5 mmol, 0.61 g), and valeroyl chloride (mol. wt. 120.58 g/mol, d. 1.016 g/mL, 11 mmol, 1.305 mL) were added to the flask. The reaction mixture was stirred for 12 hours. The reaction was monitored by TLC (1:1 hexane:ethyl acetate) to observe the disappearance of the ISMN. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane yielded a yellow oil (2.39 g, 87%) mol. wt. 275.26 g/mol.

Isosorbide-2-valeroate

Isosorbide 2-valeroate-5-mononitrate (mol. wt. 275.26 g/mol, 8.7 mmol, 2.39 g) was dissolved in acetic acid (20 mL) in a 100 mL round bottomed flask. Zinc powder (mol. wt. 65 g/mol, 87 mmol, 5.643 g) was added to the flask. The mixture was stirred for 6 hours. The reaction was monitored by TLC (1:1 hexane:ethyl acetate) to observe the disappearance of the Isosorbide 2-valeroate-5-mononitrate. Once complete, the reaction mixture was filtered through cotton wool to remove the catalyst. Ethyl acetate was then added to the reaction mixture and following this the mixture was washed with 1M HCl (50 mL), saturated sodium bicarbonate solution (50 mL), saturated brine solution (50 mL) and dried with anhydrous sodium sulphate (1 g). Evaporation of the ethyl acetate yielded a white powder (1.50 g, 75%) mol. wt. 230.26 g/mol.

Isosorbide 2-valeroate-5-nicotinate

Isosorbide 2-valeroate (mol. wt. 230.26 g/mol, 4.34 mmol, 1 g) was dissolved in dichloromethane (50 mL) in a 100 mL round bottomed flask. Triethylamine (mol. wt. 101.19 g/mol, d. 0.7255 g/mL, 18.24 mmol, 2.53 mL) and nicotinoyl chloride hydrochloride (mol. wt. 178.02 g/mol, 9.548 mmol, 1.7 g) were added to the flask. The reaction mixture was stirred at room temperature for 24 hours. The reaction was monitored by TLC (1:1 hexane:ethyl acetate) to observe the disappearance of the starting material. Once complete, the mixture was washed with 1M HCl (50 mL), saturated sodium bicarbonate solution (50 mL), saturated brine solution (50 mL) and dried with anhydrous sodium sulphate (1 g). The crude product was then dissolved in DCM and purified by column chromatography, using hexane and ethyl acetate (1:1) as eluent. Once the solvent was evaporated off, the mixture was recrystallized with diethyl ether to yield a white crystalline powder (0.3 g, 22%) mol. wt. 321.33 g/mol. $^1$H NMR (CDCl$_3$) δ: 0.91 (t, J=7.32 Hz, 3 H, H18) 1.27-1.40 (m, 2 H, H17) 1.60 (quin, J=7.63 Hz, 2 H, H16) 2.32 (t, J=7.32 Hz, 2 H, H15) 3.89-4.12 (m, 4 H, H1/6) 4.54 (d, J=4.88 Hz, 1 H, H3) 4.98 (t, J=5.19 Hz, 1 H, H4) 5.25 (d, J=3.05 Hz, 1 H, H2) 5.42 (q, J=5.49 Hz, 1 H, H5) 7.36-7.45 (m, 1H, H12) 8.33 (dd, J=7.94, 1.83 Hz, 1H, H13) 8.76-8.85 (m, 1H, H11) 9.19-9.29 (m, 1 H, H9). $^{13}$C NMR ppm (CDCl$_3$): 13.32, 21.84, 26.55, 33.52, 70.28, 73.22, 74.58, 76.36, 76.68, 77.31, 80.59, 85.85, 123.07, 136.95, 150.53, 153.27, 164.22, 172.50.

Isosorbide 2-benzoate-5-mononitrate

Isosorbide mononitrate (mol. wt. 191.139 g/mol, 10 mmol, 1.91 g) was dissolved in dichloromethane (50 mL) in a 100 mL round bottomed flask. Triethylamine (mol. wt. 101.19 g/mol, d. 0.7255 g/mL, 11 mmol, 1.52 mL), 4-Dimethylaminopyridine (mol. wt. 122.17 g/mol, 5 mmol, 0.61 g), and benzoyl chloride (mol. wt. 140.57 g/mol, d. 1.211 g/mL, 11 mmol, 1.74 mL) were added to the flask. The reaction mixture was stirred at room temperature for 12 hours. The reaction was monitored by TLC (1:1 hexane: ethyl acetate) to observe the disappearance of the ISMN. Once complete, the mixture was washed with 1M HCl (50 mL), saturated sodium bicarbonate solution (50 mL), saturated brine solution (50 mL) and dried with anhydrous sodium sulphate (1 g). Evaporation of the dichloromethane and crystallisation with diethyl ether yielded a white powder (2.5 g, 84.7%) mol. wt. 295.25 g/mol.

Isosorbide-2-benzoate

Isosorbide 2-benzoate-5-mononitrate (mol. wt. 295.25 g/mol, 8.47 mmol, 2.5 g) was dissolved in ethyl acetate (20 mL) in a 100 mL round bottomed flask. A spatula tip full of 10% palladium on activated carbon was added to the solution. Air was expelled from the flask and the mixture was kept under an atmosphere of hydrogen gas. The mixture was stirred for 12 hours. The reaction was monitored by TLC (1:1 hexane:ethyl acetate) to observe the disappearance of the Isosorbide 2-benzoate-5-mononitrate. Once complete, the reaction mixture was filtered through a fritted glass funnel to remove the catalyst. The solvent was evaporated under vacuum and crystallised using diethyl ether to give a white powder (1.92 g, 90.5%) mol. wt. 250.25 g/mol.

Isosorbide 2-benzoate-5-nicotinate

Isosorbide 2-benzoate (mol. wt. 250.25 g/mol, 6.4 mmol, 1.6 g) was dissolved in dichloromethane (50 mL) in a 100 mL round bottomed flask. Triethylamine (mol. wt. 101.19 g/mol, d. 0.7255 g/mL, 14.08 mmol, 1.95 mL), 4-Dimethylaminopyridine (mol. wt. 122.17 g/mol, 0.64 mmol, 0.078 g) and nicotinoyl chloride hydrochloride (mol. wt. 178.02 g/mol, 7.04 mmol, 1.254 g) were added to the flask. The reaction mixture was stirred at room temperature for 24 hours. The reaction was monitored by TLC (1:1 hexane: ethyl acetate) to observe the disappearance of the starting material. After 24 hours, additional triethylamine (mol. wt. 101.19 g/mol, d. 0.7255 g/mL, 7.04 mmol, 0.975 mL), DMAP (mol. wt. 122.17 g/mol, 0.64 mmol, 0.078 g), and nicotinoyl chloride hydrochloride (mol. wt. 178.02 g/mol, 3.52 mmol, 0.627 g) were added to ensure completion of the reaction. Once complete, the mixture was washed with 1M HCl (50 mL), saturated sodium bicarbonate solution (50 mL), saturated brine solution (50 mL) and dried with anhydrous sodium sulphate (1 g). The crude product was then dissolved in DCM and purified by column chromatography, using hexane and ethyl acetate (1:1) as eluent. Once the solvent was evaporated off, the mixture was recrystallized with diethyl ether to yield a white crystalline powder (1.2 g, 52.8%) mol. wt. 355.35 g/mol. $^1$H NMR (CDCl$_3$) δ: 4.01-4.19 (m, 4 H, H1/6) 4.70 (d, J=4.88 Hz, 1 H, H3) 5.09 (t, J=5.19 Hz, 1 H, H4) 5.42-5.53 (m, 2 H, H2/5) 7.40-7.50 (m, 3 H, H12/17/19) 7.54-7.65 (m, 1 H, H18) 7.98-8.07 (m, 2 H, H16/20) 8.35 (dt, J=7.94, 1.83 Hz, 1 H, H13) 8.82 (d, J=3.66 Hz, 1 H, H11) 9.28 (s, 1 H, H9). $^{13}$C NMR ppm (CDCl$_3$): 70.33, 73.17, 74.64, 76.36, 76.68, 77.99, 80.70, 85.91, 123.07, 128.12, 129.05, 129.40, 133.10, 136.91, 150.62, 153.37, 164.31, 165.22.

Isosorbide-2-aspirinate-5-nicotinate (JG or ST0702)

Isosorbide-2-aspirinate (0.3 g, 0.98 mmol), in dichloromethane (20 mL) at 0° C. was stirred for 10 mins in the presence of DCC (0.2 g, 0.98 mmol) and DMAP (0.12 g, 0.98 mmol). The reaction vessel was allowed to warm to room temperature, and nicotinic acid (0.12 g, 0.98 mmol) was added and allowed to stir for 24 hours. The reaction mixture was washed with HCl (20 mL, 1M), saturated aqueous NaHCO$_3$ (20 mL), water (3×20 mL), dried over anhydrous Na$_2$SO$_4$ and solvent removed in vacuo to give product as a crude oil (0.95 g). Purification by column chromatography over silica gel using dichloromethane and ethyl acetate (95:5) as eluent yielded the title compound as white crystals (0.12 g, 29.7%): m.pt. 94-96° C. IR$_{\nu max}$ (KBr): 3327.6 (N═C), 2929.6 (C—H stretching), 1731.7 and 1718.7 (C═O), 1654.4 (C═C stretching), 180.7 and 1195.9 (C(O)OR aromatic), 1090.4 (C—O—C) cm$^{-1}$. HRMS: Requires: 436.1008 (M$^+$+23), Found: 436.1011 (M$^+$+23). $^1$H NMR δ (CDCl3): 2.36 (3H, s, OCOCH$_3$), 4.11 (9H, m, ISI-H$_2$[α+β] and IS6-H$_2$[α+β]), 6.64 (1H, d, J 4.52 Hz, ISH-3), 5.05 (1H, t, J 5.04 and 5.52 Hz, ISH-4), 5.46 (2H, dd, J 2.0 and 2.52 Hz, ISH-5 and ISH-2), 7.11 (1H, d, J 8.52 Hz, Ar$_1$H-2), 7.32 (1H, q, J 6.52, 8.04 and 8.52 Hz, Ar$_1$H-3), 7.43 (1H, q, J 6.53, 8.04 and 8.52 Hz, Ar$_1$H-5), 7.59 (1H, t, J 6.04 and 6.52 Hz, Ar$_1$H-4), 8.00 (1H, dd, J 1.52 and 2.0 Hz, Ar$_2$H-5), 8.34 (1H, m, Ar$_2$H-6), 8.82 (1H, dd, J 2.0 and 1.48 Hz, Ar₂H-4), 9.28 (1H, d, J 2.0 Hz, Ar₂H-2). ¹³C NMR ppm (CDCl3): 20.52 (OCO$\underline{C}$H₃), 79.32 (ISC-1), 72.75 (ISC-6), 74.38 (ISO$\underline{C}$(O)Ar), 74.43 (ISC-5), 78.27 (ISC-4), 80.60 (ISC-2), 85.60 (ISC-3), 122.26 (Ar₁C-1), 122.88 (Ar₁C-4), 123.38 (Ar₂C-4), 125.57 (Ar₁C-6), 131.35 (Ar₂C-6), 133.83 (Ar₁C-2), 136.68 (Ar₁C-3), 150.55 (Ar₂C-5), 153.30 (Ar₂C-1), 164.13 (Ar₁C-5), 164.13 (Ar₂C-3), 170.59 (Ar$\underline{C}$OOR).

Isosorbide-2-aspirinate-5-isonicotinate (ST0703)

Isosorbide-2-aspirinate 17 (0.2 g, 0.65 mmol) was dissolved in dichloromethane (20 mL) at 0° C. to which was added DCC (0.13 g, 0.65 mmol) and DMAP (0.08 g, 0.65 mmol). After 10 mins the reaction vessel was returned to room temperature and iso-nicotinic acid (0.08 g, 0.65 mmol) was added and stirred for 24 hours. The reaction was washed with HCl (20 mL, 1M), saturated aqueous NaHCO₃ (20 mL), water (3×20 mL), dried over anhydrous MgSO₄ and solvent removed in vacuo to yield the title compound as a white powder (0.17 g, 63.1%): m.pt. 86-88° C. IR$_{\nu max}$ (KBr): 3327.8 (N=C), 2929.3 (C—H stretching), 1751.8 and 1710.7 (C=O), 1628.0 (C=C stretching), 1249.0 and 1194.1 (C(O)OR aromatic), 1082.8 (C—O—C) cm⁻¹. HRMS: Requires: 436.1008 (M⁺+23), Found: 436.1004 (M⁺+23). ¹H NMR δ (CDCl3): 2.37 (3H, s, OCOCH₃), 4.09 (5H, m, ISI-H₂[α+β] and IS6-H₂[α+β]), 4.65 (1H, d, J 4.52 Hz, ISH-3), 5.05 (1H, t, J 5.52 and 5.04 Hz, ISH-4), 5.46 (2H, dd, J 5.52 and 5.04 Hz, ISH-5 and ISH-2), 7.12 (1H, d, J 7.04 Hz, A₁H-2), 7.33 (1H, m, Ar₁H-3), 7.59 (2H, t, J 6.04 and 6.04 Hz, Ar₁H-5 and Ar₁H-4), 7.90 (1H, d, J 5.04 Hz, Ar₂H-6), 8.01 (1H, dd, J 2.0 and 1.52 Hz, Ar₂H-2), 8.84 (1H, s, Ar₂H-5), 8.98 (1H, s, Ar₂H-3).

Isosorbide-2-aspirinate-5-salicylate (ISAS, or ST0701)

2-benzyloxybenzoic acid (364.8 mg=1.6 mmol) was dissolved in dry DCM (20 mls) and stirred. Isosorbide-2-aspirinate (500 mg=1.6 mmol) and 10% DMAP were added. The flask was cooled to 0° C. and DCC (340 mg, 1.6 mmol) was added. Stirring was continued for five minutes and the temperature was allowed to come to room temperature. The reaction mixture was stirred overnight. The reaction was filtered and the filtrate was washed with 0.1M HCl, 5% NaHCO₃ and water, dried over sodium sulfate and volatiles were removed under reduced pressure to provide an oil. The oil was purified by column chromatography hexane/ethyl acetate (2:1) to give a white product (Rf=0.4, 228 mg). This was dissolved in methanol/ethyl acetate (1:1). Pd/C was added and the reaction was stirred under hydrogen overnight. The reaction mixture was filtered and concentrated. The resulting oil was purified by column chromatography using hexane/ethyl acetate (1:1) to yield a white solid (107 mg Rf=0.67).). ¹H NMR δ (CDCl₃) 400 MHz: 2.38 (3H, s, OCOC$\underline{H}$₃), 4.02 (4H, m, ISH-1, ISH-1', ISH-6 and ISH-6'), 4.63 (1H, d, ISH-3), 5.03 (1H, t, ISH-4), 5.43 (2H, dd, ISH-2, ISH-5), 6.91 (1H, t, Ar—H), 7.01 (1H, d, Ar—H), 7.1 (1H, d, Ar—H), 7.28 (1H, t, Ar—H), 7.48 (1H, t, Ar—H), 7.53 (1H, t, Ar—H), 7.89 (1H, d, ArH), 8.00 (1H, d, ArH), 10.61 (1H, s, OH). ¹³C NMR ppm δ (CDCl₃): 20.51 (OCO$\underline{C}$H3), 70.46 (ISC-1), 72.78 (ISC-6), 74.31 (ISC-5), 77.91 (ISC-2), 80.69 (ISC-4), 85.70 (ISC-3), 117.30 (Ar2 C-I), 118.90, 123.41, 125.65, 129.47, 131.42, 133.94, 135.65, 150.24 (Ar₁C-2), 163.12 (ArOCOCH3), 168.87 (Ar $\underline{C}$(O)OR).

Isosorbide-2-salicylate-5-nicotinate (ST0702sal)

ST0702sal can be made by a variety of methods. One convenient way for manufacturing same is to treat ST0702 with fetal calf serum which contains bovine esterases. The esterases de-acetylate the ST0702 providing ST0702sal, which may be isolated by flash chromatography.

ST0702sal can also be manufactured by the following route:

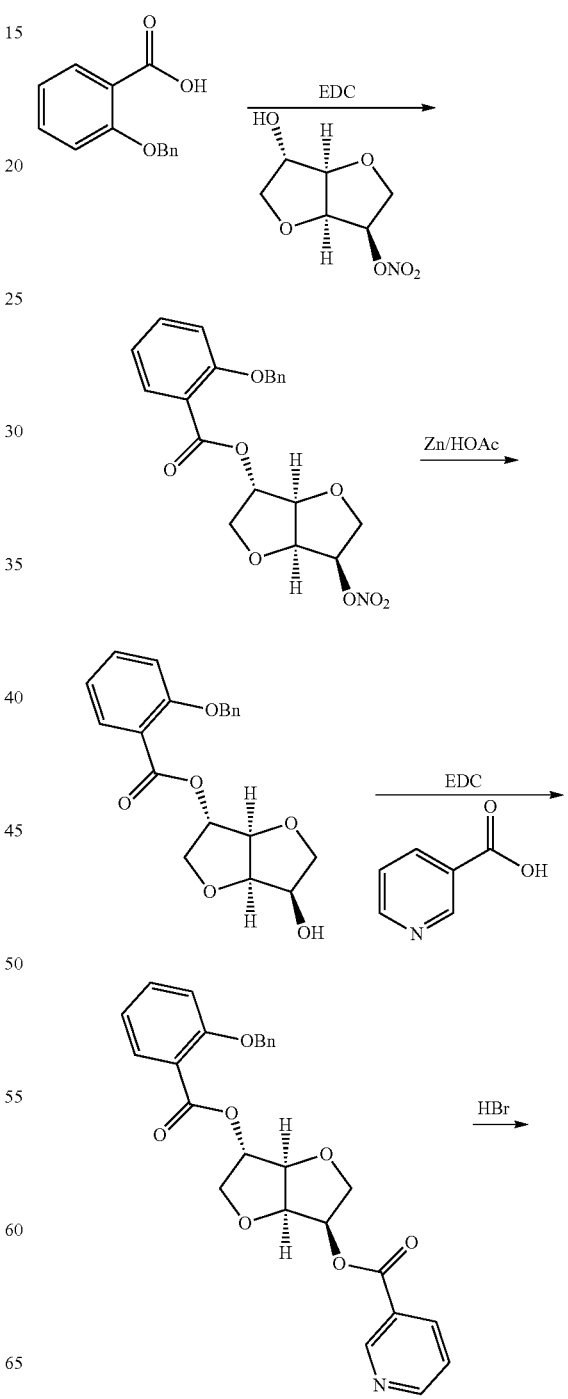

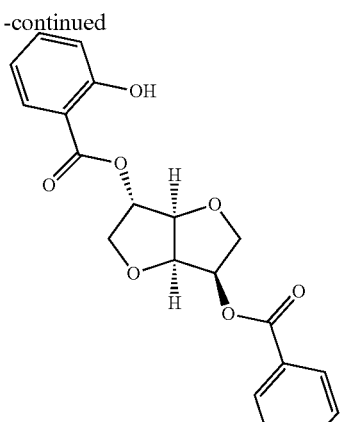

ST0702sal

Log P Calculations

The partition coefficient (P) is used to describe the lipophilicity of a drug. It is defined as the ratio of equilibrium concentrations of a drug in an organic phase ($C_{org}$) and an aqueous phase ($C_{aq}$).

$$P = \frac{C_{org}}{C_{aq}}$$

Most commonly the organic solvent is n-octanol and the other solvent is water. Hydrophobic molecules will have a high P value while hydrophilic molecules will have a low P value.

Rm values were calculated from Rf values that were obtained at three different mobile phase compositions (40, 50 and 60% MeOH in water).

The Rm value was calculated using the following equation:

$$Rm = \log\left(\frac{1}{R_f} - 1\right)$$

The theoretical Rm value at 0% organic modifier was calculated by extrapolating from the calibration curves that were obtained. These values were then correlated to the literature log P of two reference compounds (methyl benzoate and paracetamol).

TABLE 1

| Compound | 40% MeOH | | 50% MeOH | | 60% MeOH | |
|---|---|---|---|---|---|---|
| | Rf | Rm | Rf | Rm | Rf | Rm |
| ISMN (isosorbide mononitrate) | 0.6060 | −0.1870 | 0.6530 | −0.2746 | 0.7000 | −0.3680 |
| Isosorbide-2-Acetate-5-nicotinate | 0.2860 | 0.3973 | 0.3730 | 0.2256 | 0.5200 | −0.0348 |
| Isosorbide-2-Propionate-5-nicotinate | 0.1600 | 0.7202 | 0.2730 | 0.4254 | 0.4400 | 0.1047 |
| Isosorbide-2-Butyrate-5-nicotinate | 0.1060 | 0.9260 | 0.2067 | 0.5841 | 0.3530 | 0.2631 |

TABLE 1-continued

| Compound | 40% MeOH | | 50% MeOH | | 60% MeOH | |
|---|---|---|---|---|---|---|
| | Rf | Rm | Rf | Rm | Rf | Rm |
| Isosorbide-2-Valeroate-5-nicotinate | 0.0530 | 1.2521 | 0.1200 | 0.8653 | 0.2730 | 0.4254 |
| Isosorbide-2-Benzoate-5-nicotinate | 0.0260 | 1.5736 | 0.0870 | 1.0210 | 0.2060 | 0.5860 |
| ST0702 | 0.0460 | 1.3168 | 0.1200 | 0.8653 | 0.2730 | 0.4254 |
| Methyl Benzoate | 0.1460 | 0.7671 | 0.1867 | 0.6391 | 0.3600 | 0.2499 |
| Paracetamol | 0.5460 | −0.0801 | 0.6270 | −0.2256 | 0.7460 | −0.4679 |

Calculated Log P values for compounds disclosed herein are provided in Table 2.

| Compounds | Log P (ref) | Extrapolated Rm (y value) | Log P (calculated) |
|---|---|---|---|
| ISMN | | 0.176 | −0.333 |
| Isosorbide-2-Acetate-5-nicotinate | | 1.2763 | 1.3369 |
| Isosorbide-2-Propionate-5-nicotinate | | 1.9553 | 2.367 |
| Isosorbide-2-Butyrate-5-nicotinate | | 2.2483 | 2.8118 |
| Isosorbide-2-Valeroate-5-nicotinate | | 2.9143 | 3.8225 |
| Isosorbide-2-Benzoate-5-nicotinate | | 3.5292 | 4.7555 |
| STO702 | | 3.0977 | 4.1008 |
| Methyl Benzoate | 2.2 (1) | 1.845 | 2.2 |
| Paracetamol | 0.48 (2) | 0.7116 | 0.48 |

(1) Sangster et al. J. Phys. Chem. Ref. Data, Vol. 18, No. 3, 1989
(2) Machatha et al. Int. J. Pharm 2005, 294, 185

Experimental Methods

Mice

Specific Pathogen-Free female C57BL/6J strain mice, 6-8 weeks of age, were obtained from a commercial supplier and bred in-house (JAX, Charles River). Mice were fed irradiated diet and housed in individually ventilated cages (Tecniplast, UK) under positive pressure. All animal experiments were performed in compliance with the Health Products Regulatory Authority and approved by the Trinity College Dublin's BioResources ethical review board.

Psoriasis Model

The Aldara-induced model of psoriasis was used (Flutter and Nestle, 2013; Morwietz, 2015; Russell et al., 2013; van der Fits et al., 2009). The dorsal skin of mice was shaved and depilated on day −1. Mice were that were in the telogen phase (resting phase) of the hair cycle were chosen for experiments. Mice with visual skin damage from shaving were excluded. Mice were then randomly divided into groups for treatment with topical application of vehicle (white petroleum jelly) or Solvotrin test compounds, prepared in white petroleum jelly. On day 0, mice were scored for disease signs, as per below. After which 62.5 mg of Aldara™ cream (5% Imiquimod; MEDA Pharmaceuticals) was applied to a defined area of the shaved dorsal skin surface. Thirty minutes after the Aldara application, test compounds or vehicle was applied to the dorsal flank, to cover the entire Aldara-challenged surface, with an even layer of the white petroleum. This process was repeated for a further 5 days. Mice were scored daily. On day 6 the mice were euthanized for tissue collection.

Clinical Scoring of Mice

The skin of mice was scored for signs of psoriasis-like inflammation for a total of 7 days, (i.e. days 0-6), as described (van der Fits et al., 2009). Mice were scored according to 3 parameters: erythema (the redness of skin); thickening of the skin; and scaling (dryness and flaking of the skin). For each parameter, the mice were scored on a scale from 0-4. Mice with no pathology were scored 0. Mice with mild pathology scored 1. A score of 2 showed moderate pathology. A score of 3 showed marked pathology, evident pronounced disease for the given parameter. A score of 4 showed very severe pathology. The total, or Psoriasis Area and Severity Index (PASI), score was the cumulative score of all three parameters. Therefore for each mouse studied the PASI score can range between 0 to 12.

Statistical Analysis

Power calculations on data from previous studies have shown that a sample size of at least 6 will detect significant difference (P<0.05) in PASI scores between groups. ANOVA and Dunnett Multiple Comparison Test determined statistical differences between multiple groups. Two tailed Student's t-test was used to compare statistical differences between two groups.

Unless otherwise specified percentage concentration of a test compound in a composition refers to the weight percent of said test compound in the composition. For example, application of 2% compound X, means application of a composition comprising 2 weight percent of compound X.

Evaluation of Therapeutic Efficacy of ST0702 in the Aldara-Induced Model of Psoriasis in Mice.

Figure 7:
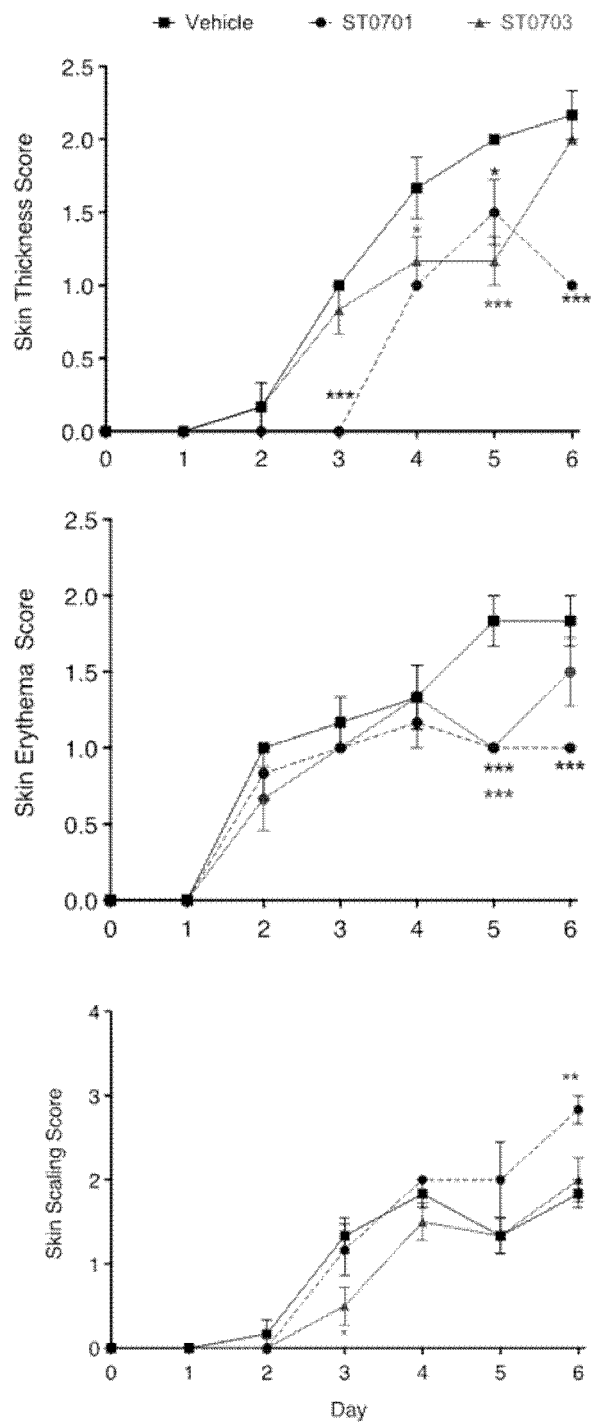
FIG. 7: Skin scaling, erythema and thickness scores of Aldara-treated mice exposed to Vehicle, ST0701 or ST0703.
Figure 8:
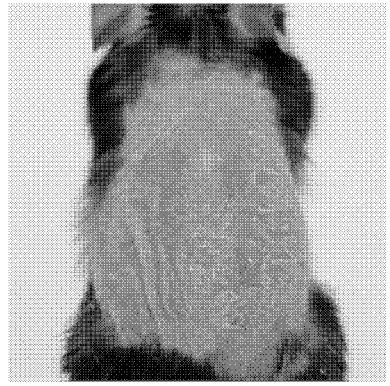
FIG. 8: Representative photographs of the shaved back skin of Aldara-treated mice exposed to Vehicle, 3% ST0701 or 3% ST0703.
Figure 8:
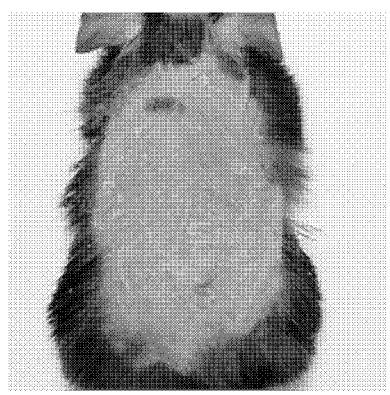
Figure 8:
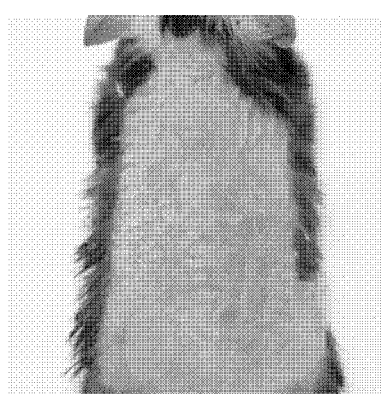
Figure 10:
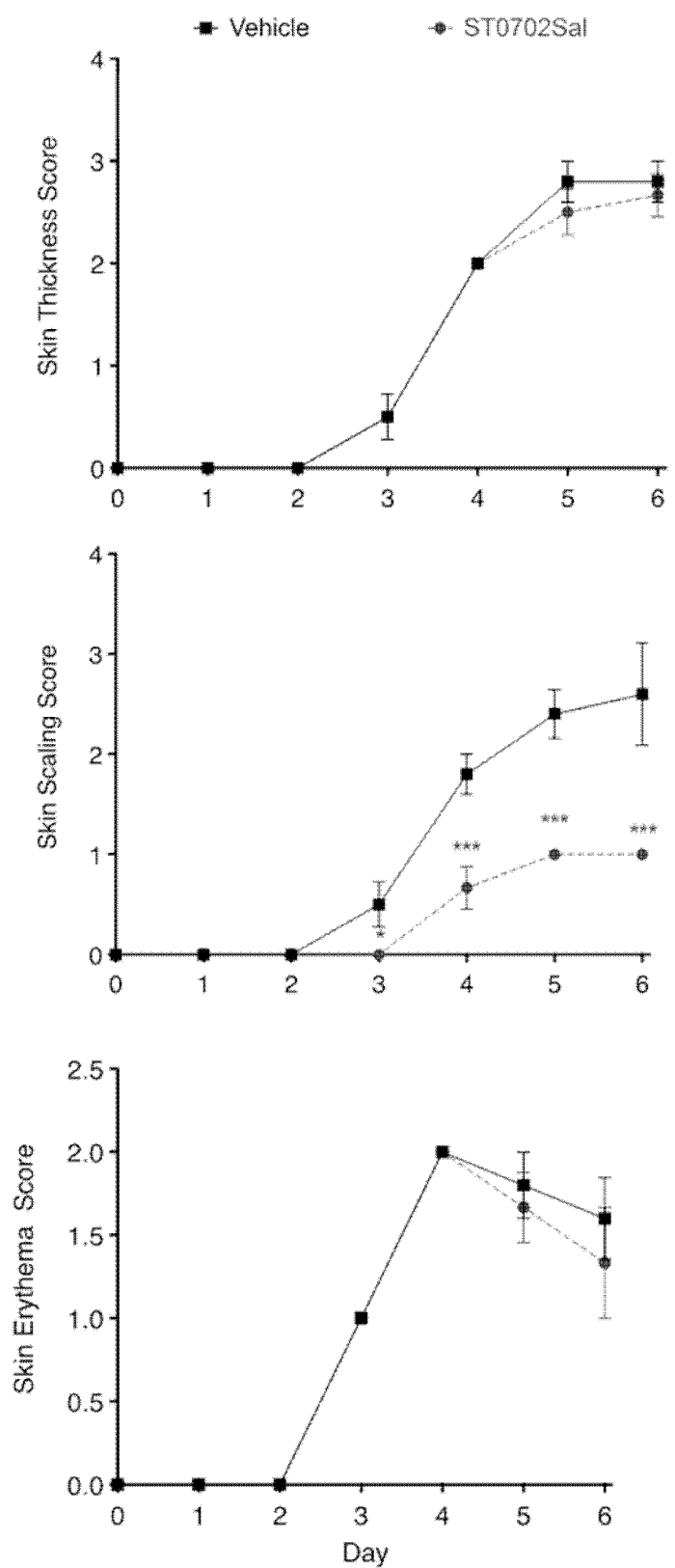
FIG. 10: Skin scaling, erythema and thickness scores of Aldara-treated mice exposed to Vehicle or ST0702Sal.
Figure 11:
FIG. 11: Representative photographs of the shaved back skin of Aldara-treated mice exposed to Vehicle or ST0702Sal
Figure 11:
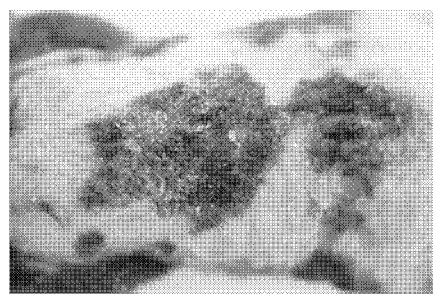
Figure 11:
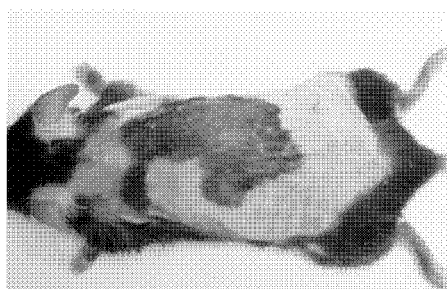
Figure 11:

In the model used following the topical application of Aldara cream to the dorsal skin of mice signs of psoriasis develop at the site of treatment. In mice co-treated with Vehicle there is a progressive increase in PASI scores, reflecting the development of erythema, skin thickening, dryness and scaling of the skin (FIGS. 1-11). Images of the site of application of Aldara to the dorsal skin show the gross appearance of these signs of psoriasis (FIGS. 5, 8, 11).

Figure 2:
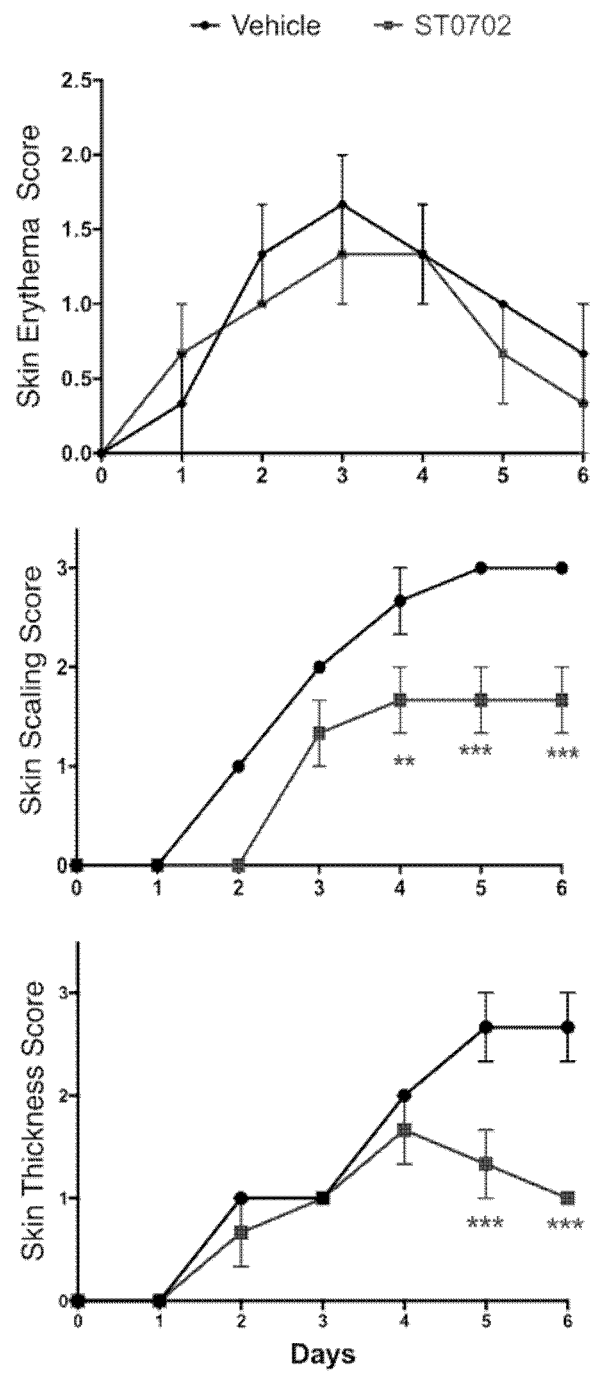
FIG. 2: Skin scaling, erythema and thickness scores of Aldara-treated mice exposed to Vehicle or 3% ST0702.
Figure 3:
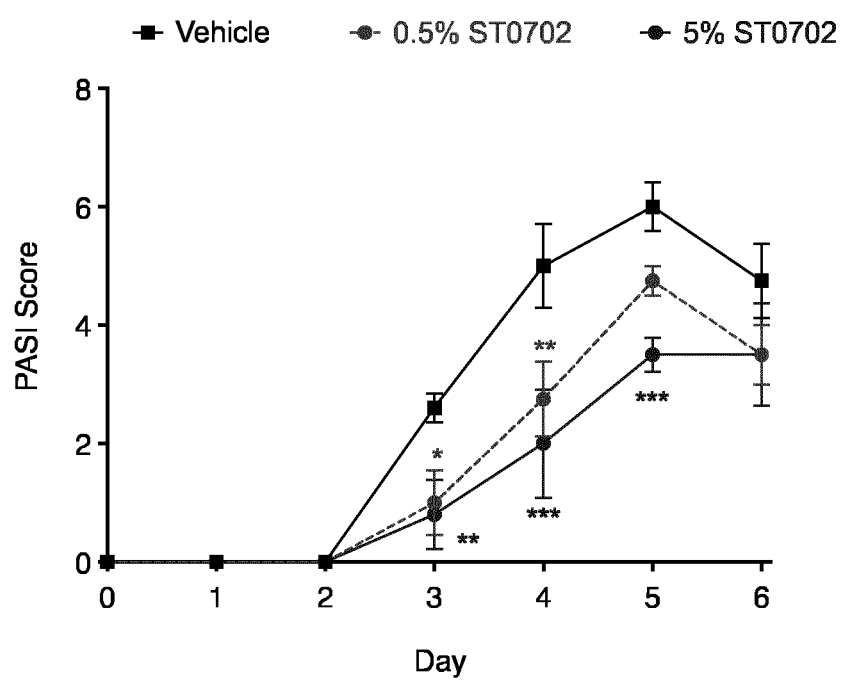
FIG. 3: Psoriasis Area and Severity Index (PASI) score of Aldara-treated mice exposed to Vehicle, 0.5 or 5% ST0702.
Figure 4:
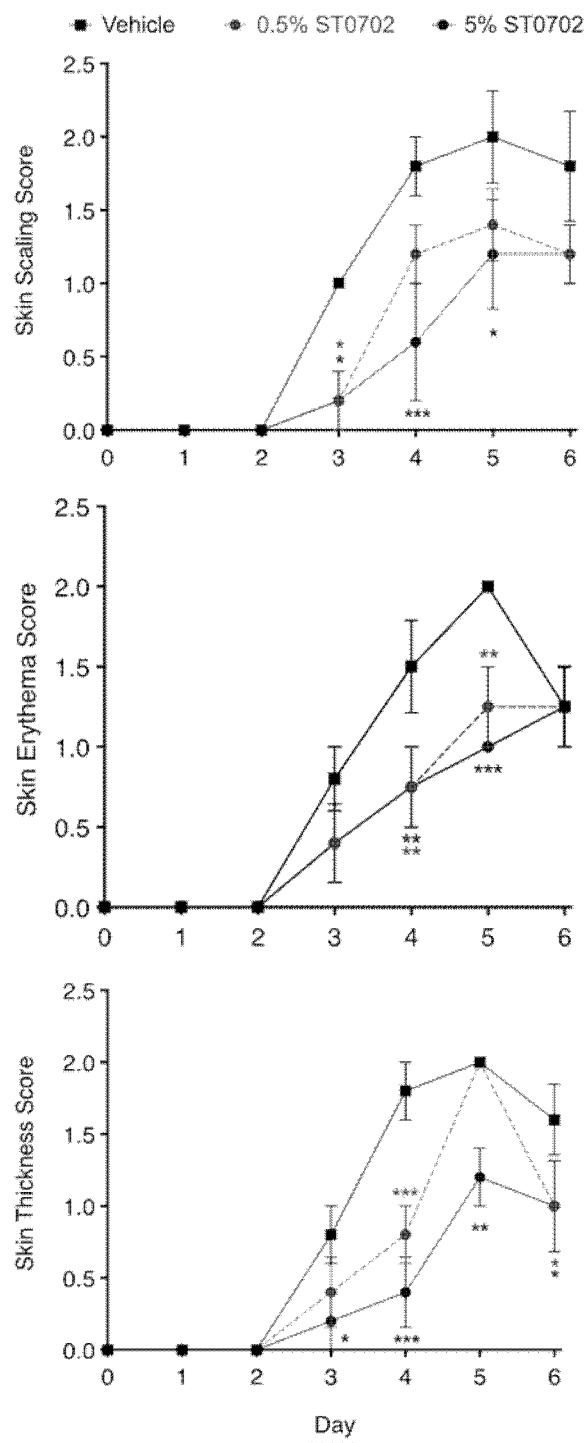
FIG. 4: Skin scaling, erythema and thickness scores of Aldara-treated mice exposed to Vehicle, 0.5 or 5% ST0702.
Figure 5:
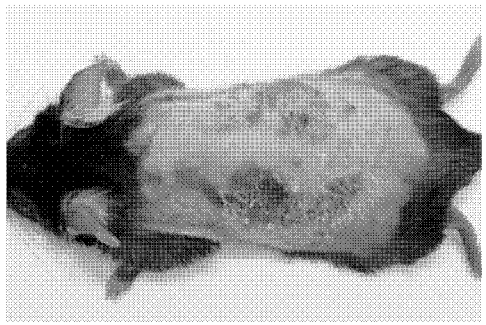
FIG. 5: Representative photographs of the shave back skin of Aldara-treated mice exposed to Vehicle, 0.5 or 5% ST0702.
Figure 5:
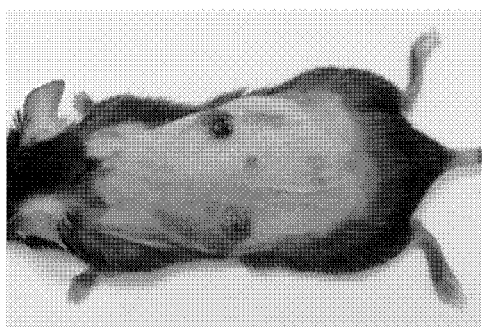
Figure 5:
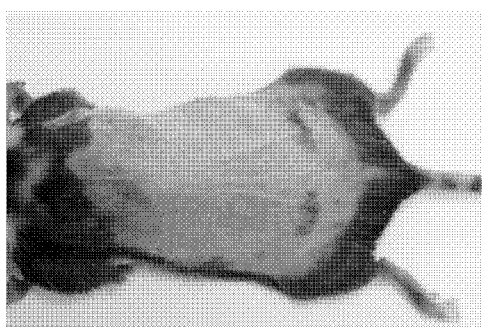

Application of ST0702 to the skin significantly (P<0.05-0.001) reduced the progressive development of psoriasis-like skin inflammation in mice in two separate experiments (FIGS. 1-4). Furthermore, the activity of ST0702 suppressed the development of signs of psoriasis in a dose-dependent manner (FIG. 3). At the lower dose of ST0702 (0.5%) PASI scores were significantly lower on days 3 (P<0.05) and 4 (P<0.01) relative to Vehicle-treated mice (FIG. 3). The higher dose of ST0702 reduced skin inflammation on days 3-5 (P<0.01-0.001) (FIG. 3). Mice treated with ST0702 had significant, and dose-dependent, reductions in the development of all three parameters of skin inflammation, skin thickness, erythema and scaling (FIG. 4). Gross pictures of the skin of Aldara-treated mice demonstrate the ameliorated disease in ST0702-treated mice (FIG. 5).

FIG. 1: Psoriasis Area and Severity Index (PASI) score of Aldara-treated mice exposed to Vehicle or 3% ST0702 (i.e. 3 wt % ST0702). ANOVA and Dunnett's multiple comparisons test was used to test for statistical differences between groups. Statistical differences between Vehicle group and ST0702 group are shown. *** P<0.001. Data are Mean and SEM from 3 mice per group.

FIG. 2: Skin scaling, erythema and thickness scores of Aldara-treated mice exposed to Vehicle or 3% ST0702. ANOVA and Dunnett's multiple comparisons test was used to test for statistical differences between groups. Statistical differences between Vehicle group and ST0702 group are shown. *** P<0.001. Data are Mean and SEM from 3 mice per group.

FIG. 3: Psoriasis Area and Severity Index (PASI) score of Aldara-treated mice exposed to Vehicle, 0.5 or 5% ST0702. ANOVA and Dunnett's multiple comparisons test was used to test for statistical differences between groups. Statistical differences between Vehicle group and 0.5 (*) and 5% (*) ST0702 groups are shown. * <0.05;  P<0.01; * P<0.001. Data are Mean and SEM from 6 mice per group.

FIG. 4: Skin scaling, erythema and thickness scores of Aldara-treated mice exposed to Vehicle, 0.5 or 5% ST0702. ANOVA and Dunnett's multiple comparisons test was used to test for statistical differences between groups. Statistical differences between Vehicle group and 0.5% (*) and 5% (*) ST0702 groups are shown. * <0.05;  P<0.01; * P<0.001. Data are Mean and SEM from 6 mice per group.

FIG. 5: Representative photographs of the shave back skin of Aldara-treated mice exposed to Vehicle, 0.5 or 5% ST0702.

Evaluation of Efficacy of ST0701 and ST0703 in the Aldara-Induced Model of Psoriasis in Mice.

Figure 6:
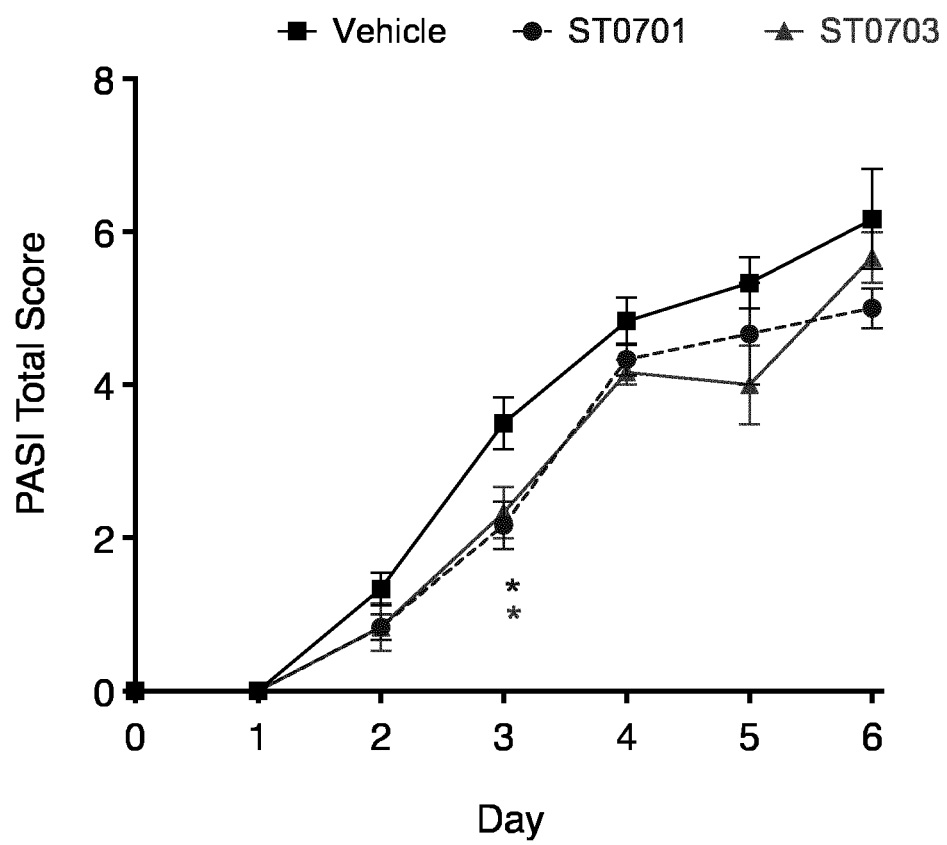
FIG. 6: Psoriasis Area and Severity Index (PASI) score of Aldara-treated mice exposed to Vehicle, ST0701 or ST0703.

The application of 3% ST0701 or 3% ST0703 in petroleum jelly both reduced the PASI scores in mice relative to Vehicle-treated animals (FIG. 6). The difference in reduction in disease signs was only statistically significant (P<0.05) for both compounds on day 3 compared to Vehicle (FIG. 6). Treatment of mice with either of the compounds reduced levels of elevated skin thickness and erythema (FIG. 7). Gross images of mouse backs demonstrated the more marked reductions in erythema of compound treated mice when compared to Vehicle-treated mice (FIG. 8).

FIG. 6: Psoriasis Area and Severity Index (PASI) score of Aldara-treated mice exposed to Vehicle, ST0701 or ST0703. ANOVA and Dunnett's multiple comparisons test was used to test for statistical differences between groups. Statistical differences between Vehicle group and ST0701 (*) and ST0703 (*) groups are shown. * <0.05. Data are Mean and SEM from 6 mice per group.

FIG. 7: Skin scaling, erythema and thickness scores of Aldara-treated mice exposed to Vehicle, ST0701 or ST0703. ANOVA and Dunnett's multiple comparisons test was used to test for statistical differences between groups. Statistical differences between Vehicle group and ST0701 (*) and ST0703 (*) groups are shown. * <0.05. Data are Mean and SEM from 6 mice per group.

FIG. 8: Representative photographs of the shaved back skin of Aldara-treated mice exposed to Vehicle, 3% ST0701 or 3% ST0703.

Evaluation of Efficacy of ST0702Sal in the Aldara-Induced Model of Psoriasis in Mice.

Figure 9:
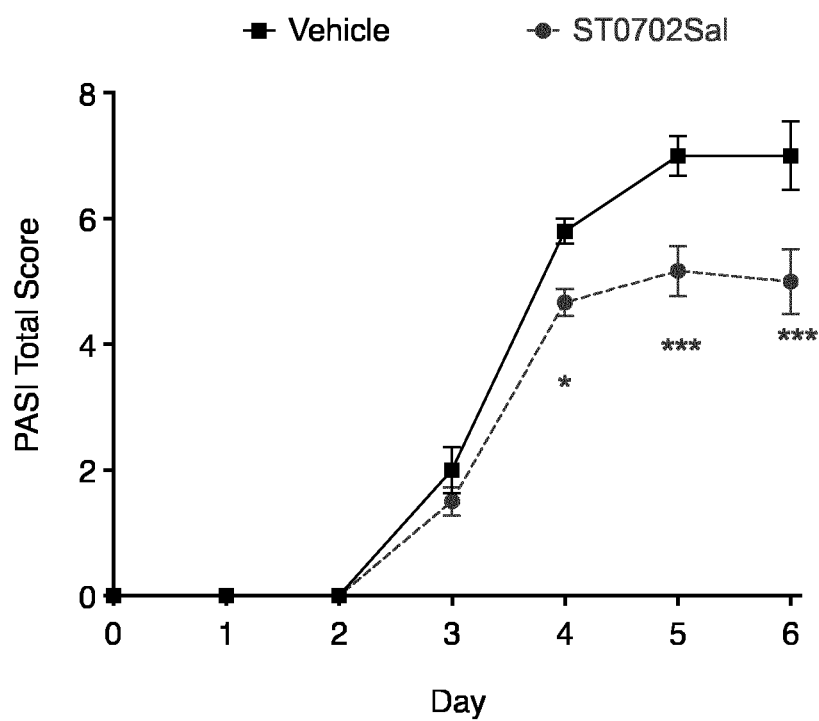
FIG. 9: Psoriasis Area and Severity Index (PASI) score of Aldara-treated mice exposed to Vehicle or ST0702Sal.

The application of ST0702Sal in petroleum jelly significantly reduced the PASI scores in mice relative to Vehicle-treated animals on days 4, 5 and 6 (FIG. 9). While Aldara-induced scaling was significantly (P<0.001) reduced in ST0702Sal-treated mice, erythema and skin thickness were not altered (FIG. 10). Advantageously, the reduced scaling on skin of mice treated with ST0702Sal was evident compared to Vehicle-treated mice (FIG. 11).

FIG. 9: Psoriasis Area and Severity Index (PASI) score of Aldara treated mice exposed to Vehicle or ST0702Sal. ANOVA and Dunnett's multiple comparisons test was used to test for statistical differences between groups. Statistical differences between Vehicle group and ST0702Sal group are shown. * <0.05; *** P<0.001. Data are Mean and SEM from 6 mice per group.

FIG. 10: Skin scaling, erythema and thickness scores of Aldara-treated mice exposed to Vehicle or ST0702Sal. ANOVA and Dunnett's multiple comparisons test was used to test for statistical differences between groups. Statistical differences between Vehicle group and ST0702Sal group are shown. <0.05; *** P<0.001. Data are Mean and SEM from 6 mice per group.

FIG. 11: Representative photographs of the shaved back skin of Aldara-treated mice exposed to Vehicle or ST0702Sal.

Figure 12:
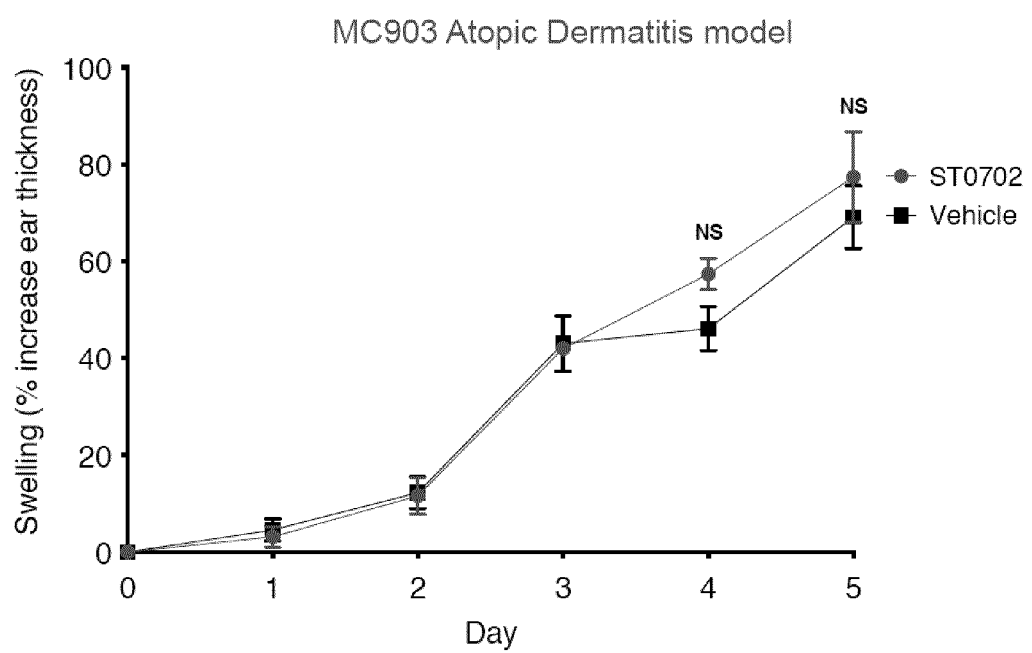
FIG. 12: Efficacy of ST0702 in the calcipotriol induced model of atopic dermatitis in mice was evaluated in comparison to vehicle.

Evaluation of Efficacy of ST0702 in the Calcipotriol Induced Model of Atopic Dermatitis in Mice FIG. 12: Efficacy of ST0702 in the calcipotriol induced model of atopic dermatitis in mice was evaluated in comparison to vehicle. (Salimi et al. J. Exp. Med. 2013, 210(13), 2939-50, & Li et al. Proc. Natl. Acad. Sci. USA. 2006, 103, 11736-11741).

MC903 (Calcipotriol) was dissolved in ethanol and mice were treated daily for 5 consecutive days as described (Salimi et al.). MC903 (25 µL of 4 nmol) was applied to the dorsal surface of both ears, every 24 hours, for 5 days. Mice were randomly divided into groups for treatment with topical application of vehicle (white petroleum jelly) or test compounds, prepared in white petroleum jelly. Test compounds or vehicle was applied to dorsal ear surface daily, 20 minutes following MC903 treatment, to cover the entire MC903 challenged surface with an even layer of the white petroleum. Ear thickness was measured daily prior to MC903 challenge. Ear data is presented as the percentage change in ear thickness, over the baseline ear thickness, with the average taken between both ears.

The effect of test compounds was comparable with vehicle. This demonstrates that the compounds of the invention selectively inhibit inflammatory pathways relevant to skin disease and are useful for the treatment of psoriasis.

Isolation and Stimulation of Peripheral Blood Mononuclear Cells (PBMCs) and Primary Human Dendritic Cells (DC):

PBMC were isolated from leukocyte-enriched buffy coats obtained from anonymous healthy donors with consent from the Irish Blood Transfusion Service, St James' Hospital, Dublin, Ireland. PBMC were pre-treated with test compounds or a vehicle control at the indicated concentrations for 6 hours prior to stimulation by anti-CD3 for 4 days and re-stimulated with PMA and ionomycin for 6 hours. Thereafter cells were counted using flow cytometry.

Primary human DC were produced from CD14+ monocytes isolated from healthy human PBMC via magnetic cell sorting. Monocyte-derived DC were pre-treated with test compounds or a vehicle control for 6 hours prior to stimulation by LPS for 24 hours. Cytokine concentrations in cell supernatants were determined by ELISA (eBiosciences).

FIGS. 13 and 14 outline the effect of treatment with test compounds and vehicle on cytokine levels monocyte-derived DC respectively.

Figures 13A, 13B, 13C, 13D, 13E:
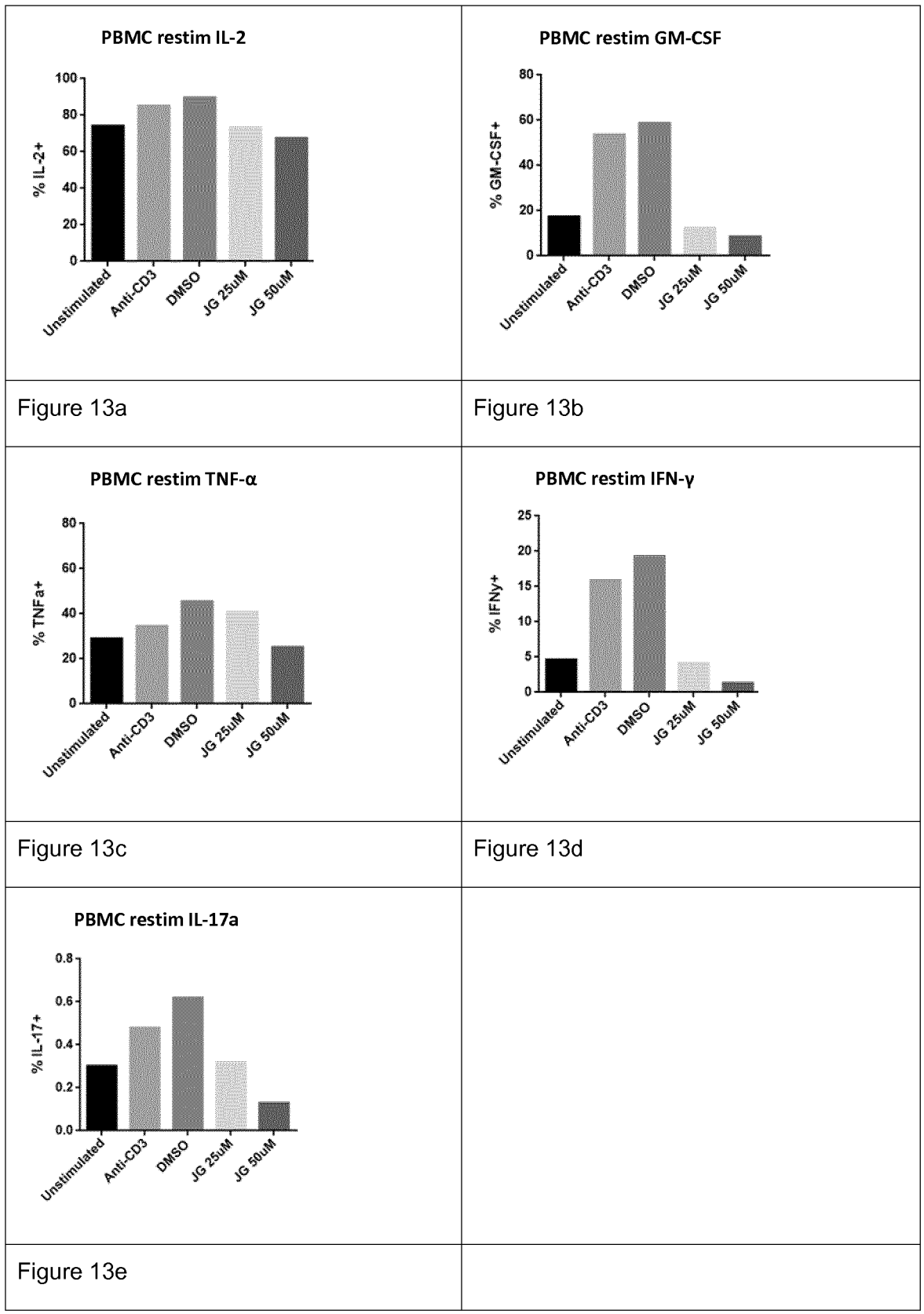
FIG. 13a-e: Inhibition of key cytokines in psoriasis progression, derived from activated T-cells by ST0702 at various concentrations.

FIG. 13*a-e*: Inhibition of key cytokines in psoriasis progression derived from activated T-cells by ST0702 at various concentrations. In FIG. 13*a* ST0702 (also called JG) is shown not to have any appreciable effect on IL-2. As IL-2 is associated with proliferation, the inhibitory effect on psoriasis promoting cytokines is not likely to be due to an effect on proliferation. FIG. 13*b* shows the appreciable effect that ST0702 had on the pro-inflammatory cytokine GM-CSF. Thus the compounds of the invention suppress the expression of GM-CSF. TNF-alpha and IFN-gamma are regarded as a significant driver of psoriasis, and their inhibition is predictive of a clinical effect. Treating PBMC with test compound at 50 µM reduced the percentage of TNF-alpha expressing cells. Similarly treating PBMC with test compound significantly reduced the percentage of IFN-gamma expressing cells in comparison to control. IL-17 is an important player in psoriasis and the test compound had an inhibitory effect on the number of IL-17 expressing cells. The fact that the expression of select cytokines is inhibited by the compounds of the invention, suggests that the compounds are selectively blocking important inflammatory pathways in psoriasis.

Figures 14A, 14B:
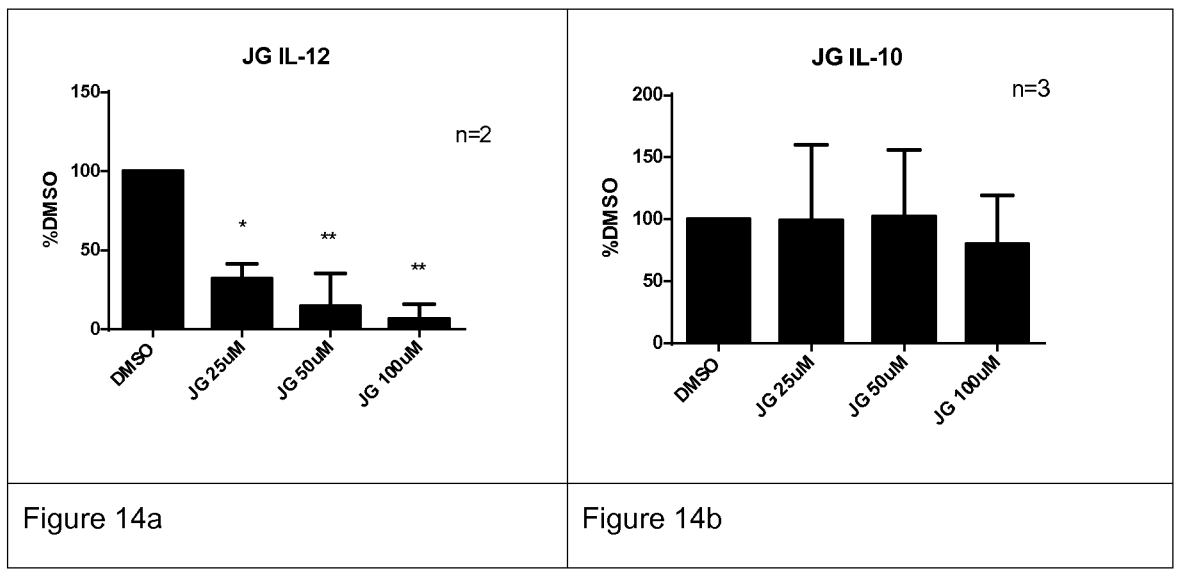
FIG. 14: Inhibition of key cytokines in psoriasis progression, derived from activated dendritic cells.

FIG. 14: FIG. 14*a* shows the effect of ST0702 on IL-12 concentration. ST0702 treatment exerted similar effects on another key psoriasis cytokine, IL23 (data not shown). FIG. 14*b* shows that ST0702 has no appreciable effect on IL-10, an anti-inflammatory cytokine. This is predictive of a protective effect.

Assessment of Erythema and Itchiness

Test article dispersed in petroleum jelly was applied to a 2×2 cm patch of shaved forearm (n=3). At specified time intervals the degree of erythema was recorded by blinded observers on a scale of 1-4 (n=3). Itchiness was observed by scratching behaviour also by blinded observers on a scale of 1-4. The time course of erythema resolution was recorded at 30 minute intervals.

Figure 15:
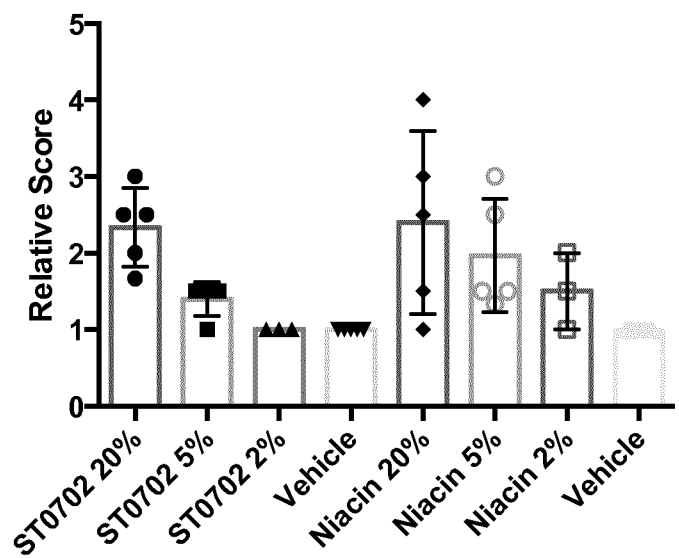
FIG. 15: Assessment of erythema and irritation after 1 hour of application of varying concentrations of ST0702, niacin or vehicle to normal healthy skin.

FIG. 15 shows erythema response to ST0702 (JG) versus niacin following application in the concentration range 2-20%. Notably, at 2% a concentration at which it was effective in the ALDARA model, and under conditions in which it is expected to release niacin, ST0702 application did not cause erythema/irritation. $p<0.05$ vs 5%; *$p<0.05$ vs vehicle. Likert scale 1-5 normalised to vehicle.

Figure 16:
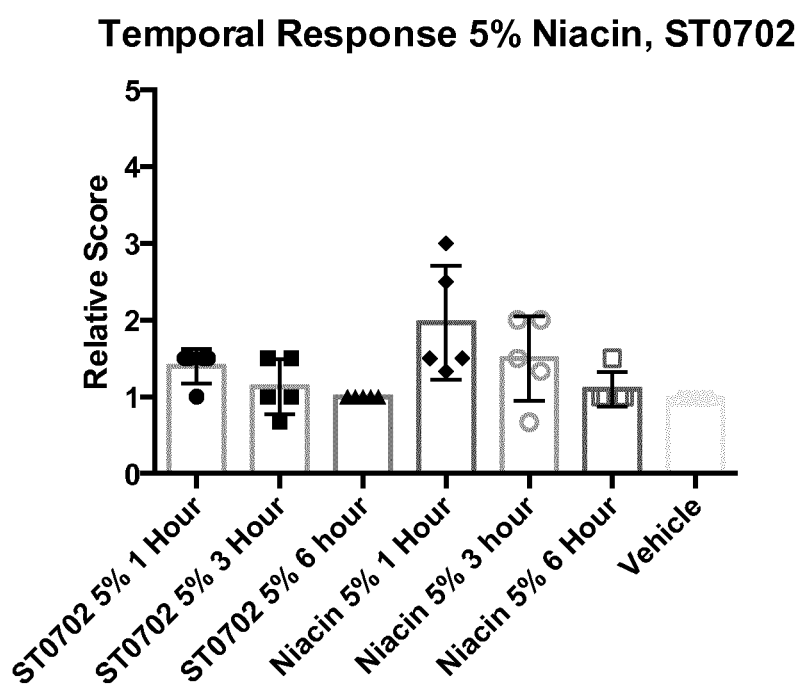
FIG. 16: Assessment of transient erythema in response to application of 5% niacin, 5% ST0702 and vehicle to normal healthy skin.

FIG. 16: shows the temporal erythema response to ST0702 or niacin both at 5%. Erythema persisted in the niacin case up to six hours whereas it resolved rapidly in the case of ST0702. ***$p<0.05$ vs vehicle. Likert scale 1-5 normalised to vehicle.

Figure 17:
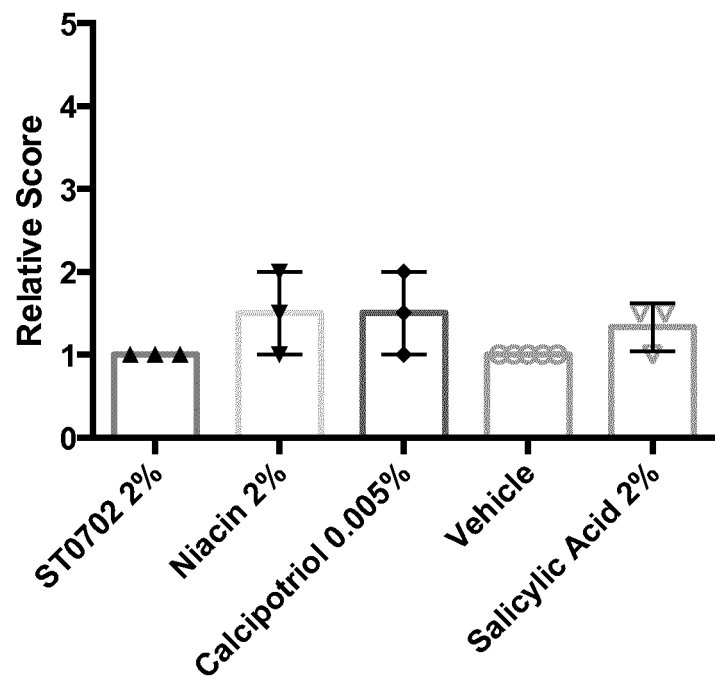
FIG. 17: Assessment of erythema in response to application of 2% ST0702, 2% niacin, 0.005% calcipotriol, 2% salicylic acid and vehicle to normal healthy skin.

FIG. 17: shows the cumulative irritancy score for ST0702 (2%), calcipitriol (0.005%), and salicylic acid (2%). ST0702 did not cause irritancy/erythema whereas the other two test articles, at their clinically used concentration did cause erythema. Likert scale 1-5 normalised to vehicle.

RESULTS

Administration of compounds of the invention, to mice in the Aldara-induced model of psoriasis (murine imiquimod psoriasis) significantly inhibits, by multiple parameters the development and progression of skin inflammation. The suppression of psoriasis-like inflammation by compounds of the invention, occurs in a dose dependent manner. Control experiments indicate that the presence of the nicotinate moiety in the compounds of the invention is critical to their efficacy. In particular, ST0701 and ST0703 which comprise aspirinate and isonicotinate moieties in the 5-isosorbide position, did not inhibit inflammation in the mouse psoriasis model. Interestingly, ST0701 is the most effective aspirin prodrug reported to date, accordingly, the anti-psoriatic effect observed by the compounds of the invention cannot be directly linked to the compounds ability to release aspirin. Moreover, the effect observed for the compounds of the invention, cannot be directly linked to the compounds ability to produce salicylic acid, since ST0701, which comprises two salicylic acid moieties, is ineffective. Equally, the effects may not be attributed to niacin, a potential byproduct of metabolism of the compounds in skin, because niacin causes skin irritation. Without being bound by theory, the compounds of the invention themselves, rather than their metabolites appear to be directly responsible for the therapeutic effects observed. Compounds of the invention are known to be rapidly metabolised in blood, and therefore would not achieve the desired therapeutic effect if administered orally.

Keratinocyte hyperproliferation is one of the hallmarks of psoriasis and this is driven by cytokines released locally from activated T-cells. Proliferating activated keratinocytes perpetuate the inflammatory cycle by releasing pro-inflammatory cytokines, which act as chemotractants causing further recruitment of T-cells and activation of angiogenesis promoting plaque neovascularisation. IL-12 and IL-17/23 are pivotal to disease progression. CD4+ (helper) T cells can become differentiated into $T_H1$ cells (driven by IL-12) or $T_H17$ cells (driven by IL-23). The signature proinflammatory cytokines from these cell types include IFNγ, TNFα and IL-17. IL-17A is a key keratinocyte activator in psoriasis and it has emerged as an important therapeutic target. Several antibodies to IL-17A or IL-23 in clinical development have been shown to be effective to treat moderate to severe psoriasis, underpinning the biochemical understanding of the disease.

To further characterise the means by which the compounds of the invention, elicit their anti-psoriatic effect, the compounds of the invention were assessed to determine their effect on psoriasis relevant inflammatory cytokine production.

The compounds of the invention are effective in reducing multiple parameters in the imiquimod (Aldara) model of murine psoriasis. Consistent with this they exert significant inhibitory effects on cytokines widely linked with the development and progression of psoriasis namely IL12, IL17 and IL23 while preserving anti-inflammatory IL10. The compounds lack irritancy relative to their components and potential metabolites when applied to normal skin at concentrations in which they are effective in imiquimod model.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A compound having the formula:

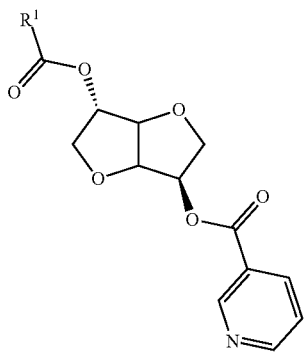

wherein $R^1$ is $C_1$-$C_{10}$ alkyl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, or a pharmaceutically acceptable salt thereof.

2. The compound as claimed in claim 1, wherein $R^1$ is selected from methyl, ethyl, propyl, butyl, pentyl and hexyl, or isomers thereof.

3. A pharmaceutical composition comprising a compound having the formula:

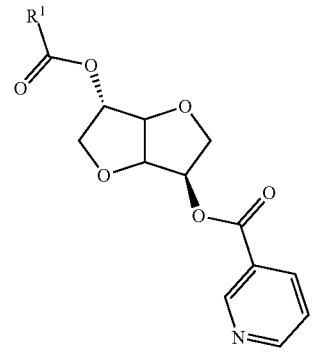

wherein $R^1$ is $C_1$-$C_{10}$ alkyl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, and a pharmaceutically acceptable carrier or excipient.

4. The pharmaceutical composition according to claim 3, wherein $R^1$ is selected from methyl, ethyl, propyl, butyl, pentyl and hexyl, or isomers thereof.

5. The pharmaceutical composition for according to claim 3, wherein said composition is for topical administration.

6. The pharmaceutical composition according to claim 3, wherein the carrier is selected from the group consisting of an ointment, cream, gel, solution, emulsion, dispersion, suspension, shampoo, paste, foam, aerosol, suppository, pad and gelled stick.

7. The pharmaceutical composition according to claim 3, wherein the compound is present in an amount of from 0.001 to 20 weight percent based on the total weight of the composition.

8. A method for treating psoriasis, the method comprising administering to a subject in need thereof a therapeutically effective amount of a compound having the formula:

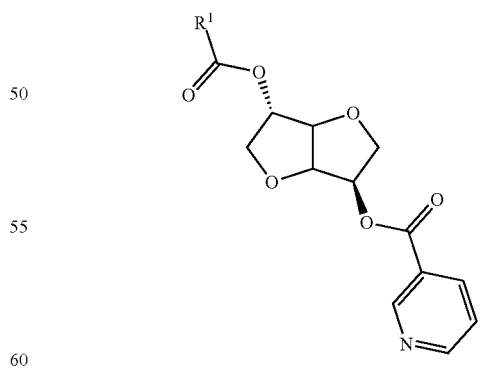

wherein $R^1$ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)$R^2$, $NR^3_2$, wherein $R^2$ is $C_1$-$C_6$ alkyl and wherein each $R^3$ is independently H or $C_1$-$C_6$ alkyl, or a pharmaceutically acceptable salt thereof.

9. The method of treatment according to claim 8, wherein the compound has the formula:

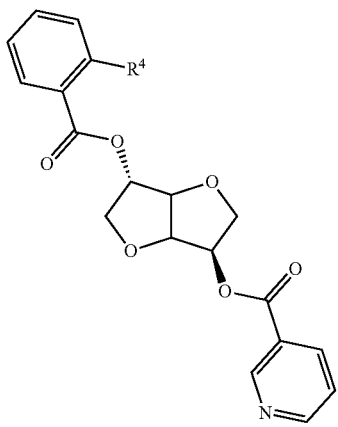

wherein R⁴ is selected from the group consisting of H, hydroxyl and —O(O)R², wherein R² is $C_1$-$C_6$ alkyl, or a pharmaceutically acceptable salt thereof.

10. The method of treatment of claim 8, wherein the compound is

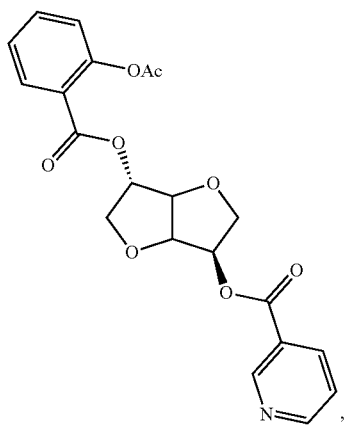 [SMILES: CC(=O)Oc1ccccc1C(=O)O[C@H]1COC2C1OC[C@H]2OC(=O)c1cccnc1]

or a pharmaceutically acceptable salt thereof.

11. The method of treatment of claim 8, wherein R¹ is selected from methyl, ethyl, propyl, butyl, pentyl and hexyl, or isomers thereof.

12. A method for treating psoriasis, the method comprising administering to a subject in need thereof a pharmaceutical composition comprising a therapeutically effective amount of a compound having the formula:

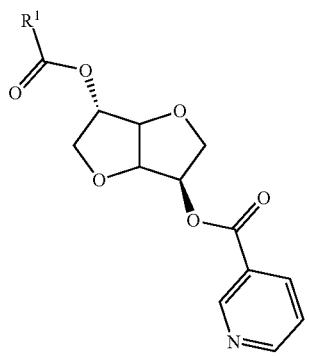

wherein R¹ is $C_1$-$C_{10}$ alkyl or $C_5$-$C_{10}$ aryl optionally substituted with one or more of hydroxyl, halo, $C_1$-$C_6$ alkyl, $C_1$-$C_6$ alkoxy, —O(O)R², NR³₂, wherein R² is $C_1$-$C_6$ alkyl and wherein each R³ is independently H or $C_1$-$C_6$ alkyl, or a pharmaceutically acceptable salt thereof.

13. The method of treatment according to claim 12, wherein the compound has the formula:

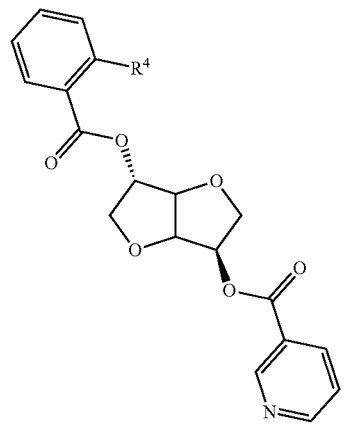

wherein R⁴ is selected from the group consisting of H, hydroxyl and —O(O)R², wherein R² is $C_1$-$C_6$ alkyl, or a pharmaceutically acceptable salt thereof.

14. The method of treatment of claim 13, wherein the compound is

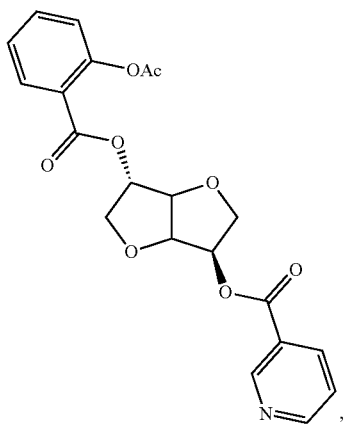 [SMILES: CC(=O)Oc1ccccc1C(=O)O[C@H]1COC2C1OC[C@H]2OC(=O)c1cccnc1]

or a pharmaceutically acceptable salt thereof.

15. The method of treatment of claim 12, wherein R¹ is selected from methyl, ethyl, propyl, butyl, pentyl and hexyl, and isomers thereof.

16. The method of treatment of according to claim 8, wherein the compound or composition is administered topically.

* * * * *